United States Patent
Wu et al.

(10) Patent No.: US 11,634,750 B2
(45) Date of Patent: Apr. 25, 2023

(54) METHODS AND COMPOSITIONS FOR PREPARING POLYNUCLEOTIDES

(71) Applicant: CYGNUS BIOSCIENCES (BEIJING) CO., LTD., Beijing (CN)

(72) Inventors: Yalei Wu, Foster City, CA (US); Wai Ho Lee, San Francisco, CA (US); Kai Qin Lao, Pleasanton, CA (US)

(73) Assignee: Cygnus Biosciences (Beijing) Co., Ltd., Beijing (CN)

( * ) Notice: Subject to any disclaimer, the term of this patent is extended or adjusted under 35 U.S.C. 154(b) by 295 days.

(21) Appl. No.: 16/823,731

(22) Filed: Mar. 19, 2020

(65) Prior Publication Data

US 2020/0283826 A1 Sep. 10, 2020

Related U.S. Application Data

(63) Continuation of application No. PCT/US2018/052217, filed on Sep. 21, 2018.

(60) Provisional application No. 62/562,332, filed on Sep. 22, 2017.

(51) Int. Cl.
*C12Q 1/68* (2018.01)
*C12Q 1/6806* (2018.01)
*C12N 9/22* (2006.01)
*C12Q 1/6844* (2018.01)

(52) U.S. Cl.
CPC ............ *C12Q 1/6806* (2013.01); *C12N 9/22* (2013.01); *C12Q 1/6844* (2013.01); *C12Y 201/01037* (2013.01)

(58) Field of Classification Search
None
See application file for complete search history.

(56) References Cited

U.S. PATENT DOCUMENTS

| | | | |
|---|---|---|---|
| 5,235,809 | A | 8/1993 | Farrell |
| 5,705,628 | A | 1/1998 | Hawkins |
| 6,210,891 | B1 | 4/2001 | Nyren et al. |
| 2011/0318739 | A1 | 12/2011 | Santourlidis |
| 2013/0217071 | A1 | 8/2013 | Montesclaros et al. |
| 2014/0135234 | A1 | 5/2014 | Williams et al. |
| 2014/0363815 | A1* | 12/2014 | Dahl ............ C12Q 1/6869 435/6.11 |
| 2015/0299767 | A1 | 10/2015 | Armour et al. |
| 2016/0177359 | A1* | 6/2016 | Ukanis ............ C12Q 1/6874 435/91.1 |

FOREIGN PATENT DOCUMENTS

| | | |
|---|---|---|
| WO | WO-2015089333 A1 | 6/2015 |
| WO | WO-2016061517 A2 | 4/2016 |
| WO | WO-2016101258 A1 | 6/2016 |

OTHER PUBLICATIONS

Brenner. A cultivated taste for yeast. Genome Biol. 2000;1(1):REVIEWS103. Epub Apr. 27, 2000.
Brenner, C. Chemical genomics in yeast. Genome Biology. 2004; 5:240.
Dicker, et al. The detection of TP53 mutations in chronic lymphocytic leukemia independently predicts rapid disease progression and is highly correlated with a complex aberrant karyotype. Leukemia. Jan. 2009; 23(1):117-124.
Eason, et al. Characterization of synthetic DNA bar codes in *Saccharomyces cerevisiae* gene-deletion strains. Proc Natl Acad Sci U S A. Jul. 27, 2004;101(30):11046-51. Epub Jul. 16, 2004.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
International search report with written opinion dated Apr. 3, 2019 for PCT/US2018/052217.
Kumar et al., Emerging technologies in yeast genomics. Nature Reviews Genetics 2: 302-312 (2001).
McLendon, et al. Survival analysis of presumptive prognostic markers among oligodendrogliomas. John Wiley & Sons. Oct. 15, 2005; 104(8):1693-1699.
PCT/US2018/052217 International Preliminary Reporton Patentability dated Mar. 24, 2020.
Winzeler, et al. Functional characterization of the *S. cerevisiae* genome by gene deletion and parallel analysis. Science. Aug. 6, 1999;285(5429):901-6.

* cited by examiner

*Primary Examiner* — Suryaprabha Chunduru
(74) *Attorney, Agent, or Firm* — Novick, Kim & Lee, PLLC; Allen Xue

(57) ABSTRACT

Provided herein are methods, compositions, and kits for forming amplification products. In various embodiments provided herein, transposomes comprising transposases are used in forming tagged polynucleotides for downstream amplification and polynucleotide processing steps.

24 Claims, 7 Drawing Sheets

Specification includes a Sequence Listing.

SEQUENCE LISTING

```
<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cagacgtgtg ctcttccgat ctagatgtgt ataagagaca g                    41

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgtctctta tacacatct                                             19

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acactctttc cctacacgac gctcttccga tctddddcgc gcgg                 44

<210> SEQ ID NO 4
<211> LENGTH: 58
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 4
aatgatacgg cgaccaccga gatctacact ctttccctac acgacgctct tccgatct          58

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caagcagaag acggcatacg agatgtgact ggagttcaga cgtgtgctct tccgatct          58

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acactctttc cctacacgac gctcttccga tct                                    33

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagacgtgtg ctcttccgat ctagatgtgt ataagagaca g                           41

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acactctttc cctacacgac gctcttccga tct                                    33
```

METHODS AND COMPOSITIONS FOR PREPARING POLYNUCLEOTIDES

RELATED APPLICATIONS

The present application claims priority to U.S. provisional application Ser. No. 62/562,332, filed Sep. 22, 2017, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 20, 2018, is named 53081-701_601_SL.txt and is 2,127 bytes in size.

BACKGROUND

Transposase-mediated fragmentation and tagging of polynucleotides can be used in the preparation of polynucleotides, for example in the generation of sequencing libraries. Tagmentation offers advantages of simplified sample preparation and work-flow in which polynucleotides to be sequenced can be fragmented and tagged in a single reaction. These resulting polynucleotides can be further amplified and/or subjected to sequence specific selection prior to sequencing. Sequence information of polynucleotides can be used to identify sequence variants for diagnostic, therapeutic, forensic, and many other applications.

Simple and rapid sample preparation can be useful for analyzing polynucleotide samples. Polynucleotide samples can be processed in parallel or in bulk, for example, in a high-throughput multiplexing. However, the existing method for preparing nucleic acid samples often suffer from a number of drawbacks. Amongst them are low yields and non-specific amplification resulting from primer dimer products.

SUMMARY

In view of the foregoing, there is a need for improved methods for forming amplification products. The methods and compositions provided herein address this need, and provide additional advantages as well.

In an aspect, the present disclosure provides a method of forming amplification products of a target polynucleotide, comprising: (a) contacting a target polynucleotide present in a polynucleotide sample with transposomes to yield a plurality of tagged fragments, individual transposomes comprising a transposase complexed with a transposon sequence having a transposon element, wherein a given tagged fragment of the plurality comprises a transposon sequence joined to the 5' end of a segment of the target polynucleotide; (b) subjecting the plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, wherein a given extension product comprises (i) a sequence of the given tagged fragment and a complement of an extension primer sequence, or (ii) a complement of the given tagged fragment sequence and the extension primer sequence; and (c) amplifying the extension products using a primer pair to yield amplification products, the primer pair including a first primer comprising the transposon sequence or a portion thereof and a second primer comprising the sequence of the segment at the 5' end of the extension primer or a portion thereof, wherein individual amplification products comprise a single copy of the transposon sequence or a complement thereof.

In some embodiments, the segment at the 3' end of individual extension primers lacks sequence complementarity to the transposon sequence. In some embodiments, the segment at the 3' end of individual extension primers comprises a gene specific sequence. In some embodiments, the extension primers comprise a mixture of gene-specific extension primers. In some embodiments, the mixture of gene-specific extension primers target at least two genes. In some embodiments, the extension primers share an identical segment at the 5' end. In some embodiments, the extension primers comprise methylated cytosines.

In some embodiments, the extension products comprise hemi-methylated double-stranded DNA. In some embodiments, the method further comprises, subsequent to (b), subjecting the extension products comprising hemi-methylated double-stranded DNA to a methylation reaction to yield extension products comprising fully methylated double-stranded DNA. In some embodiments, methylation is effected by methyl transferase activity. In some embodiments, methylation is effected by a DNA methyltransferase enzyme. In some embodiments, the DNA methyltransferase enzyme is DNA (cytosine-5)-methyltransferase 1 (DNMT1).

In some embodiments, the method further comprises, prior to (c), subjecting the extension products comprising fully methylated double-stranded DNA to cytosine deamination to convert unmethylated cytosines to uracil. In some embodiments, cytosine deamination is effected by bisulfate or apolipoprotein B mRNA editing enzyme, catalytic polypeptide-like (APOBEC).

In some embodiments, the polynucleotide is a cell-free polynucleotide. In some embodiments, the polynucleotide is a genomic polynucleotide. In some embodiments, the polynucleotide sample is obtained from a formalin-fixed paraffin-embedded (FFPE) tissue sample. In some embodiments, the polynucleotide sample is obtained from a frozen tissue sample. In some embodiments, the polynucleotide sample is obtained from a biological fluid.

In some embodiments, the transposon sequence comprises methylated cytosines. In some embodiments, the transposase is a Tn transposase, an MuA transposase, or a Vibhar transposase. In some embodiments, the transposase is a Tn transposase selected from Tn3, Tn5, Tn7, and Tn10. In some embodiments, individual transposomes comprise a dimer of monomers, individual monomers comprising a transposase complexed with a transposon sequence.

In some embodiments, at least one of the first and second primers of the primer pair comprises a barcode sequence, an amplification primer binding sequence, a sequencing primer binding sequence, or combinations thereof. In some embodiments, the amplifying of (c) is effected by a Hot-Start enzyme. In some embodiments, the Hot-Start enzyme is a Hot-Start polymerase.

In an aspect, the present disclosure provides a method of selectively amplifying a polynucleotide comprising methylated 'CG' tandems, wherein the polynucleotide comprising methylated 'CG' tandems is present in a sample of polynucleotides having methylated and unmethylated 'CG' tandems, comprising: (a) contacting the sample with transposomes to yield a plurality of tagged fragments, individual transposomes comprising a transposase complexed with a transposon sequence having methylated cytosines, wherein a given tagged fragment of the plurality comprises a transposon sequence joined to the 5' end of a segment of a polynucleotide of the sample; (b) subjecting the plurality of tagged fragments to cytosine deamination to convert unmethylated cytosine residues of the plurality of tagged fragments to uracil; (c) subjecting the plurality of tagged fragments to an extension reaction using extension primers to yield extension products, individual extension primers having a segment at a 3' end exhibiting sequence complementarity to 'CG' tandems present in tagged fragments and a segment at a 5' end lacking sequence complementarity to tagged fragments, wherein the segment at the 3' end lacks sequence complementarity to 'UG' tandems present in tagged fragments resulting from cytosine deamination of unmethylated cytosine residues in (b), and wherein individual extension products comprise (i) a tagged fragment sequence and a complement of a primer sequence, or (ii) a complement of a tagged fragment sequence and a primer sequence; and (d) amplifying the extension products using a primer pair to yield amplification products, the primer pair including a first primer comprising the transposon sequence or a portion thereof and a second primer comprising the sequence of the segment at the 5' end of the extension primer or a portion thereof, wherein a given amplification product comprises a single copy of the transposon sequence or a complement thereof, thereby preferentially amplifying the polynucleotide comprising methylated 'CG' tandems.

In some embodiments, cytosine deamination is effected by bisulfite or apolipoprotein B mRNA editing enzyme, catalytic polypeptide-like (APOBEC).

In some embodiments, the segment at the 3' end of individual extension primers comprises the sequence CGCGCGG, CGCGCGA, CGCGCGT, CGCGCGC, CGGCGCGG, CGGCGCGA, CGGCGCGT, CGGCGCGC, CGCGGCGG, CGCGGCGA, CGCGGCGT, CGCGGCGC, CGGCGGCGG, CGGCGGCGA, CGGCGGCGT, or CGGCGGCGC. In some embodiments, the segment at the 3' end of individual extension primers comprises the sequence CGCGCGG.

In some embodiments, the sample comprises cell-free polynucleotides. In some embodiments, the sample comprises genomic polynucleotides. In some embodiments, the sample is obtained from a formalin-fixed paraffin-embedded (FFPE) tissue sample. In some embodiments, the sample is obtained from a frozen tissue sample. In some embodiments, the sample is obtained from a biological fluid.

In some embodiments, the transposase is a Tn transposase, an MuA transposase, or a Vibhar transposase. In some embodiments, the transposase is a Tn transposase selected from Tn3, Tn5, Tn7, and Tn10. In some embodiments, individual transposomes comprise a dimer of monomers, individual monomers comprising a transposase and a transposon sequence.

In some embodiments, at least one of the first and second primers of the primer pair comprises a barcode sequence, an amplification primer binding sequence, a sequencing primer binding sequence, or combinations thereof. In some embodiments, the amplifying of (d) is effected by a Hot-Start enzyme. In some embodiments, the Hot-Start enzyme is a Hot-Start polymerase.

In an aspect, the present disclosure provides a kit for generating extension products of a target polynucleotide, comprising: (a) a transposase; (b) a transposon sequence having a transposon element; (c) an extension primer comprising: (i) a segment at a 3' end exhibiting sequence complementarity to the target polynucleotide, and (ii) a segment at a 5' end lacking sequence complementarity to the target polynucleotide; (d) a Hot-Start polymerase; and (e) instructions for use of the kit for generating extension products of the target polynucleotide.

In some embodiments, the instructions of (d) comprise (i) contacting the target polynucleotide with a transposome to yield a tagged fragment, the transposome comprising the transposase complexed with the transposon sequence, wherein the tagged fragment comprises the transposon sequence joined to the 5' end of a segment of the target polynucleotide; (ii) subjecting the tagged fragment to an extension reaction using the extension primer to yield the extension products, wherein a given extension product comprises (i) the tagged fragment sequence and a complement of the extension primer sequence, or (ii) a complement of the tagged fragment sequence and the extension primer sequence. In some embodiments, the instructions of (d) further comprises (iii) amplifying the extension products using the primer pair to yield a plurality of amplification products, wherein individual amplification products comprise a single copy of a transposon sequence or a complement thereof.

In some embodiments, the kit comprises a mixture of gene-specific extension primers.

In some embodiments, the kit further comprises a primer pair, wherein the primer pair includes a first primer comprising the transposon sequence or a portion thereof and a second primer comprising the sequence of the segment at the 5' end of the extension primer or a portion thereof. In some embodiments, at least one of the first and second primers comprises a barcode sequence, amplification primer binding sequence, sequencing primer binding sequence, or combinations thereof.

In some embodiments, the transposase is a Tn transposase, an MuA transposase, or a Vibhar transposase. In some embodiments, the transposase is a Tn transposase selected from Tn3, Tn5, Tn7, and Tn10. In some embodiments, the transposon comprises methylated cytosines. In some embodiments, the kit further comprises at least one of bisulfite, apolipoprotein B mRNA editing enzyme, catalytic polypeptide-like (APOBEC), and DNMT1.

In an aspect, the present disclosure provides a reaction mixture for forming extension products, comprising: (a) a transposome comprising a transposase complexed with a transposon sequence; (b) a target polynucleotide; (c) an extension primer comprising: (i) a segment at a 3' end exhibiting sequence complementarity to the target polynucleotide, and (ii) a segment at a 5' end lacking sequence complementarity to the target polynucleotide; and (d) a Hot-Start polymerase.

In some embodiments, the reaction mixture further comprises a primer pair, wherein the primer pair includes a first primer comprising the transposon sequence or a portion thereof and a second primer comprising the sequence of the segment at the 5' end of the extension primer or a portion thereof. In some embodiments, at least one of the first and second primers comprises a barcode sequence, amplification primer binding sequence, sequencing primer binding sequence, or combinations thereof.

In some embodiments, the target polynucleotide is a cell-free polynucleotide. In some embodiments, the target polynucleotide is a genomic polynucleotide. In some embodiments, the target polynucleotide is obtained from a formalin-fixed paraffin-embedded (FFPE) tissue sample. In some embodiments, the target polynucleotide is obtained from a frozen tissue sample. In some embodiments, the target polynucleotide is obtained from a biological fluid.

In some embodiments, the transposon comprises methylated cytosines. In some embodiments, the transposome complex comprises a homodimer of monomers, individual monomers comprising a transposase complexed with a transposon sequence. In some embodiments, the transposase is a Tn transposase, an MuA transposase, or a Vibhar transposase. In some embodiments, the transposase is a Tn transposase selected from Tn3, Tn5, Tn7, and Tn10.

In an aspect, the present disclosure provides a system comprising: (a) a computer configured to receive a user request to perform a nucleic acid detection reaction on a polynucleotide sample; (b) one or more processors configured to execute commands that effect an amplification unit to perform a nucleic acid amplification reaction on the sample or a portion thereof in response to the user request, wherein the amplification reaction comprises the steps of: (i) contacting the polynucleotide sample with transposomes to yield a plurality of tagged fragments, individual transposomes comprising a transposase complexed with a transposon sequence, wherein a given tagged fragment of the plurality comprises a transposon sequence joined to the 5' end of a segment of a given polynucleotide of the polynucleotide sample; (ii) subjecting the plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, and wherein a given extension product comprises (i) a tagged fragment sequence and a complement of a primer sequence, or (ii) a complement of a tagged fragment sequence and a primer sequence; and (iii) amplifying the extension products using a primer pair to yield amplification products comprising a single copy of a transposon sequence or a complement thereof, wherein the primer pair includes a first primer comprising the transposon sequence, or a portion thereof, and a second primer comprising the sequence of the segment at the 5' end of the extension primer, or a portion thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
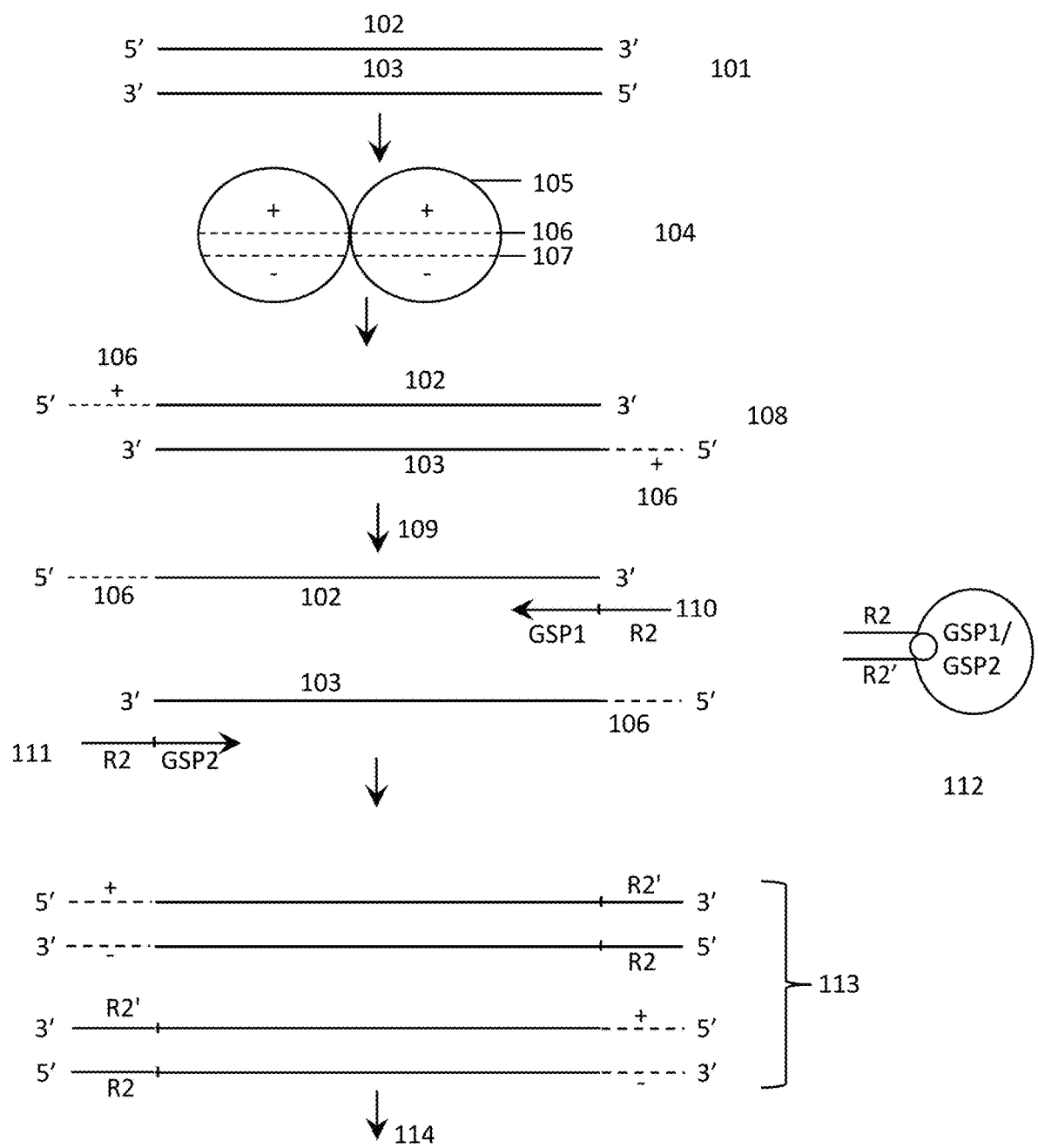
FIGS. 1A and 1B illustrate an exemplary embodiment of forming amplification products.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about," meaning within an acceptable error range for the particular value, should be assumed.

The terms "polynucleotide", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "strand," as used herein, refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. The term "bottom strand," as used herein, refers to the strand that is complementary to the "top strand."

The term "target polynucleotide," as used herein, refers to a nucleic acid molecule or polynucleotide in a starting population of nucleic acid molecules having a target sequence whose presence, amount, and/or nucleotide sequence, or changes in one or more of these, are desired to be determined. The target polynucleotide may be a portion of a larger polynucleotide (e.g. a portion to be amplified, sequenced, or otherwise analyzed), or may be used to refer to the larger polynucleotide comprising a target sequence. In general, the term "target sequence" refers to a nucleic acid sequence on a single strand of nucleic acid. The target sequence may be a portion of a gene, a regulatory sequence, genomic DNA, cDNA, fusion gene, RNA including mRNA, miRNA, rRNA, or others. The target sequence may be a target sequence from a sample or a secondary target such as a product of an amplification reaction.

A polynucleotide may have a 5' end and 3' end, referring to the end-to-end chemical orientation of a single strand of polynucleotide or nucleic acid. In a single strand of linear DNA or RNA, the chemical convention of naming carbon atoms in the nucleotide sugar-ring means that there generally exists a 5' end which frequently contains a phosphate group attached to the 5' carbon and a 3' end which typically is unmodified from the ribose —OH substituent (hydroxyl group). In some cases, a polynucleotide may have a —OH substituent or a hydroxyl group at a 5' end and —P group or phosphate group at a 3' end. A phosphate group attached to the 5'-end permits ligation of two nucleotides, e.g., the covalent binding of a 5'-phosphate to the 3'-hydroxyl group of another nucleotide, to form a phosphodiester bond. Removal of the 5'-phosphate may inhibit or prevent ligation. The 3'-hydroxyl group is also important as it is joined to the 5'-phosphate in ligation.

The term "tag," as used herein, refers to a nucleic acid molecule that provides a means of identifying the target polynucleotide fragment to which it is attached. For example, a tag can comprise a polynucleotide sequence that permits identification, recognition, and/or molecular or biochemical manipulation of the target polynucleotide to which it is attached (e.g., by providing a site for annealing an oligonucleotide, such as a primer for extension by a DNA polymerase, or an oligonucleotide for capture or for a ligation reaction). The process of attaching the tag to a polynucleotide molecule is sometimes referred to herein as "tagging" and a polynucleotide that undergoes tagging or that contains a tag is referred to as "tagged" (e.g., "tagged polynucleotide" or "tagged fragment"). For example, a tagged polynucleotide fragment (e.g., tagged fragment) can comprise a transposon having a transposon sequence as a tag.

The term "sequence variant," as used herein, refers to any variation in sequence relative to one or more reference sequences. Typically, the sequence variant occurs with a lower frequency than the reference sequence for a given population of individuals for whom the reference sequence is known. In some cases, the reference sequence is a single known reference sequence, such as the genomic sequence of a single individual. In some cases, the reference sequence is a consensus sequence formed by aligning multiple known sequences, such as the genomic sequence of multiple individuals serving as a reference population, or multiple sequencing reads of polynucleotides from the same individual. In some cases, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some cases, the sequence variant occurs with a frequency of about or less than about 0.1%. A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), insertion and/or deletion polymorphisms (INDEL), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some embodiments, a sequence variant can refer to a chromosome rearrangement, including, but not limited to, a translocation or fusion gene.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art)

to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner, optionally with default settings), the BLAST algorithm (see e.g. the BLAST alignment tool, optionally with default settings), or the Smith-Waterman algorithm (see e.g. the EMBOSS Water aligner optionally with default settings). Optimal alignment may be assessed using any suitable parameters of a chosen algorithm, including default parameters.

The term "adaptor" or "adapter," as used herein, generally refers to a nucleic acid which can be attached to another polynucleotide. For example, an adaptor can refer to a single-stranded polynucleotide which can be attached to a single-stranded polynucleotide (e.g., a cell-free polynucleotide, fragment of a cell-free polynucleotide, genomic DNA, or fragment of genomic DNA). In some cases, an adaptor can refer to a double-stranded nucleic acid which can be attached to a double-stranded nucleic acid. An adaptor can be attached to either a 5' end or a 3' end of a polynucleotide. In some cases, an adaptor can be attached to both ends of a polynucleotide, that is, one adaptor to each end.

The term "primer," as used herein, generally refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension reaction is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primers are usually first treated to separate its strands before being used to prepare extension products. This denaturation step is typically effected by heat, but may alternatively be carried out using alkali, followed by neutralization. Thus, a "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The terms "reverse primer" and "forward primer" refer to primers that hybridize to different strands in a double-stranded DNA molecule.

The term "extension product," as used herein, generally refers to a product of a reaction in which a nucleotide primer is extending by the covalent addition of nucleotides. In some cases, the nucleotide incorporation can be guided by a template. In some cases, the nucleotide incorporation can occur without a template. In some cases, an extension product is an amplification product, such as from PCR amplification, rolling circle amplification (RCA), or isothermal amplification.

The terms "amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. In some cases, the amplification is effected by means of PCR using a pair of primers. Amplified products can be subjected to subsequent analyses, including but not limited to melting curve analysis, nucleotide sequencing, single-strand conformation polymorphism assay, allele-specific oligonucleotide hybridization, Southern blot analysis, and restriction endonuclease digestion.

The terms "isolated" and "isolating," with reference to a polynucleotide or polynucleotide complex, including but not limited to ligation products and amplification products, generally refers to a preparation of the substance (e.g., polynucleotide, polynucleotide complex, ligation products and amplification products thereof) devoid of at least some of the other components that may also be present where the substance or a similar substance naturally occurs or is initially obtained from (e.g., a biological sample, a sample reaction volume, e.g., a ligation reaction volume, an amplification reaction volume etc). For example, an isolated substance may be prepared using a purification technique to enrich it from a source mixture. Enrichment can be measured on an absolute basis or in terms of a concentration, for example in terms of weight per volume of solution, molecules per volume of solution, or any other appropriate measure.

The terms "stem-loop product" and "stem-loop structure", as used herein, generally refer to a secondary structure of a polynucleotide in which intramolecular hybridization occurs between portions of the polynucleotide. A stem loop may form when two regions of a single polynucleotide strand hybridize to form a double-stranded portion, which can be referred to as a "stem," and a single-stranded loop that is unpaired, which can be referred to as a "loop". The stem can be of any variable length of base pairs, and base pairing along a stem may be interrupted internally by gaps of one or more unpaired bases on one or both portions participating in the stem. The loop can be of any variable length of unpaired bases. In some cases, the loop is at least 3 bases in length. In some cases, the two regions forming the "stem" are completely complementary. In some cases, the two regions forming the "stem" are partially complementary. In some cases, a single polynucleotide may comprise one stem loop structure. In some cases, a single polynucleotide may comprise more than one stem loop structure. The stem portion of a stem loop structure may terminate as a double stranded section with no overhangs, with a single stranded section comprising a 5' overhang, with a single stranded section comprising a 3' overhang, or with single-stranded portions extending from both the 5' end and the 3' end. A stem loop structure can also be referred to as a "hairpin" or "hairpin structure."

In various aspects, the present disclosure provides methods, reaction mixtures, kits, and systems for preparing a polynucleotide sample. Polynucleotides prepared according to the embodiments herein can be used for polynucleotide analysis, including but not limited to sequencing assays. In some embodiments, the methods are useful for preparing a polynucleotide sample comprising polynucleotides such as, but not limited to, cell-free DNA and genomic DNA.

In an aspect, the present disclosure provides a method of forming amplification products of a target polynucleotide. The method comprises (a) contacting a target polynucleotide present in a polynucleotide sample with transposomes to yield a plurality of tagged fragments, individual transposomes comprising a transposase complexed with a transposon sequence having a transposon element, wherein a given tagged fragment of the plurality comprises a transposon sequence joined to the 5' end of a segment of the target polynucleotide; (b) subjecting the plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, wherein a given extension product comprises (i) a sequence of the given tagged fragment and a complement of an extension primer sequence, or (ii) a complement of the given tagged fragment sequence and the extension primer sequence; and (c) amplifying the extension products using a primer pair to yield amplification products, the primer pair including a first primer comprising the transposon sequence (or a portion thereof) and a second primer comprising the sequence of the segment at the 5' end of the extension primer (or a portion thereof), wherein individual amplification products comprise a single transposon sequence or a complement thereof.

A plurality of tagged fragments can be formed by contacting a target polynucleotide with transposomes through the process of transposition or tagmentation. A transposome can comprise a transposase complexed with or bound to at least one transposon sequence having a transposon element, which can also referred to as a transposase element. Transposases refer to enzymes capable of complexing with at least one transposon sequence and catalyzing insertion or transposition of the transposon sequence into a target polynucleotide to yield a modified or "tagged" polynucleotide. Transposases, generally, can catalyze insertion or transposition of the transposon sequence to a target polynucleotide by a cut and paste mechanism or a replicative transposition mechanism.

Transposases applicable for the subject methods can be of prokaryotic or eukaryotic origin. Exemplary transposases include, but are not limited to, integrases, HERMES, and HIV integrases. Non-limiting examples of transposases which can be used in embodiments herein include Tn transposases (e.g. Tn3, Tn5, Tn7, Tn10, Tn552, Tn903), MuA transposases, Vibhar transposases (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, any prokaryotic transposase, or any transposase related to and/or derived from those provided herein. In some embodiments, a subject method utilizes a Tn transposase, an MuA transposase, or a Vibhar transposase. In some cases, the transposase utilized in a subject method is a Tn transposase, for example, a Tn transposase selected from Tn3, Tn5, Tn7, and Tn10. In some cases, the transposomes comprise a dimer of monomers, individual monomers comprising a transposase and a transposon sequence. The transposome dimer can be a homodimer or a heterodimer. In some cases, the transposition reaction can be facilitated and/or triggered by addition of one or more cations. The cations can be divalent cations such as, for example, $Ca^{2+}$, $Mg^{2+}$ and $Mn^{2+}$.

A transposon sequence can comprise a nucleic acid, e.g., single- and/or double-stranded nucleic acid. A transposon sequence can be a double-stranded polynucleotide, for example completely double-stranded or partially double-stranded, e.g., having a single-stranded overhang, having a bubble, having a loop, etc. A transposon sequence generally includes a transposon element or a transposase element. A transposon element or transposase element refers to a nucleic acid molecule, or portion thereof, that includes nucleotide sequences that form a transposome with a transposase or integrase enzyme. In some embodiments, a transposon element is capable of forming a functional complex (e.g., transposome) with a transposase in a transposition reaction. Non-limiting examples of transposon elements include the 19-bp outer end ("OE") transposon end, inner end ("IE") transposon end, or "mosaic end" ("ME") transposon end recognized by, for example, a wild-type or mutant Tn5 transposase, or the R1 and R2 transposon end. In some embodiments, the transposon element or transposase element of a transposon sequence used in embodiments herein is a ME transposon end. Transposon elements can comprise any nucleic acid or nucleic acid analogue suitable for forming a functional complex with the transposase or integrase. For example, the transposon element can comprise DNA, RNA, modified bases, non-natural bases, a modified backbone, or can comprise nicks in one or both strands.

During transposition or tagmentation, one strand of a double-stranded transposon sequence (e.g., "transferred strand") is covalently linked to one strand of a double-stranded polynucleotide. In some cases, the transferred strand is covalently linked to the 5' end of the one strand of the double-stranded polynucleotide. The other strand of the transposon sequence can be referred to as the "non-transferred strand." In cases where the target polynucleotide is a double-stranded polynucleotide, the top strand of the double-stranded polynucleotide can be joined to a transposon sequence via tagmentation by a first transposase while the bottom strand of the same double-stranded polynucleotide can be joined at its 5' end to a second transposon sequence via tagmentation by a second transposase.

In some cases, the transposome breaks the target polynucleotide into fragments while covalently transferring the transposon sequence to first strand of polynucleotide fragment. In cases where the transposase catalyzes insertion or transposition of the transposon sequence to the target polynucleotide by a cut and paste mechanism, the target polynucleotide may be fragmented in smaller polynucleotides (e.g., fragments).

In some cases, the transposition reaction can include fragmentation prior to tagging of the polynucleotide with the transposon. In some cases, fragmentation and tagging can occur simultaneously or substantially at the same time. In some cases, the transposase cleaves the polynucleotide to produce a staggered cut that generates overhangs. The overhangs can be 1 base pair (bp), 2 bp, 3 bp, 4 bp, 5 bp, 6 bp, 7 bp, 8 bp, 9 bp, 10 bp, or more. For example, Tn5 can cleave the polynucleotide to produce 9 bp overhangs at 5' ends of the double stranded sequence. In some cases, the transposase cleave the polynucleotide to produce a blunt end cut.

The transferred strand of a transposon sequence can remain hybridized to the non-transferred strand following tagmentation. In some embodiments, a gap between the non-transferred strand and one strand of the double-stranded target polynucleotide is formed. In some embodiments, this gap is not filled in by a polymerase and/or ligase. In some embodiments, the non-transferred strand of the transposon sequence does not remain hybridized to the transferred strand. In some embodiments, the non-transferred strand of the transposon sequence dissociates from the transferred strand, for example as a result of heat denaturation. In some embodiments, the non-transferred strand is separated from the transferred strand prior to the extension reaction.

The term "tagged fragment" can refer to either the top or bottom strand so long as the strand is covalently linked to a transposon sequence.

Insertion of a transposon sequence by a transposase can be at a random or substantially random site in a target polynucleotide. In some embodiments, a transposon sequence can include sequences in addition to a transposon element. In some embodiments, the additional sequences can be inserted into a target polynucleotide via the transposition reaction. The additional sequences can include a primer binding site, such as a sequencing primer site and/or an amplification primer site. Additional sequences can also include a cleavage site, an anchor site, a reporter tag, and a barcode. A primer binding site can include sequences for sequencing primers to anneal to a nucleic acid in a sequencing reaction or other extension reactions. Such additional sequences can be useful in downstream polynucleotide manipulation steps as well.

A tagged fragment resulting from contacting a transposase with a target polynucleotide can comprise a transposon sequence linked to the 5' end of a fragment or a portion of the target polynucleotide. In certain cases, a given tagged fragment can include a transposon sequence on a 3' end of the polynucleotide.

In some cases, following transposition, the transposase can be removed or inactivated before proceeding to the next step of a reaction. The transposase can be removed by any of a variety of suitable methods, including purification, or inactivated, for example via denaturation or enzymatic treatment. Removal of the transposase can be useful in minimizing the inhibition to downstream reactions, such as extension reactions or amplification reactions that may use tagged fragments as templates. In some cases, a chemical treatment can be employed for removing the transposase. For example, the chemical treatment can include treating the tagged fragments with a detergent solution, such as an SDS solution. In some cases, the tagged fragments are not subjected to treatment to remove the transposase.

The plurality of tagged fragments can then be subjected to an extension reaction using extension primers. The extension primers can have a segment at a 5' end and a segment at a 3' end. In some cases, the extension primers can have addition segments interposed between the 5' and 3' ends or flanking the 5' and/or 3' ends. In some cases, the segment at the 3' end exhibits sequence complementarity to a tagged fragment. In some cases, the segment at the 3' end does not exhibit sequence complementarity to the transposon sequence but rather a sequence of the target polynucleotide. In some cases, the extension primers comprised methylated nucleotides (e.g., methylated cytosines).

For example, where extension products comprising a particular gene sequence are desired for downstream analysis, the extension primer can comprise a segment at the 3' end capable of acting as a gene specific primer (e.g., having a gene specific sequence). The gene specific sequence of the extension primer can hybridize to a gene specific tagged fragment and initiate primer extension. The extension reaction can select for, and in some cases, enrich a target sequence from a plurality of tagged fragments. In some cases, extension primers having gene specific sequences corresponding to multiple genes can be used in combination to select for, and in some cases enrich, a plurality of gene specific tagged fragments. For example, to generate extension products of tagged fragments corresponding to two gene sequences (e.g., gene 1 and gene 2), half of the extension primers may have a 3' segment with a sequence specific for gene 1 and half of the extension primers may have a 3' segment with a sequence specific for gene 2. For further example, to generate extension products of tagged fragments corresponding to three gene sequences (e.g., gene 1, gene 2, and gene 3), one-third of the extension primers may have a 3' segment with a sequence specific for gene 1, one-third of the extension primers may have a 3' segment with a sequence specific for gene 2, and one-third of the extension primers may have a 3' segment with a sequence specific for gene 3. The ratios of primers in a mixture can be optimized and/or adjusted as desired.

In some cases, the gene specific sequence can include a sequence targeting a cancer specific gene or a sequence implicated in cancer. In some cases, multiple extension primers, each being specific for one target gene, are utilized. In some cases, the extension primers of a method herein comprise a mixture of gene-specific extension primers and the mixture is used, for example, for multiplex processing. In some cases, the mixture of gene-specific extension primers target at least 5 genes (e.g., at least 10 genes, 15 genes, 20 genes, 25 genes, 50 genes, 100 genes, 200 genes, 300 genes, 400 genes, 500 genes, 600 genes, 700 genes, 800 genes, 900 genes, or 1,000 genes).

In some cases, the segment at the 3' end of an extension primer may not comprise gene-specific sequences. The segment may have other sequence specificity. For example, the segment at the 3' end can have sequence complementarity to 'CG' tandems in tagged fragments.

In various embodiments, the segment at the 5' end of an extension primer lacks sequence complementarity to a tagged fragment. In some embodiments, the 5' end of an extension primer comprises sequences that may be utilized in downstream sample processing steps. For example, the segment at the 5' end of an extension primer can comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

In some embodiments, the segment at the 5' end can include sequencing primer binding sequence (e.g., Read1 or Read2), unique molecular identifiers or barcode sequences (e.g., i5, i7) and/or flow cell binding sequences (e.g., P5, P7). In some cases, all extension primers in an extension reaction share an identical segment at the 5' end. For example, the segment at the 5' end can be identical or substantially similar (e.g., having at least about 70%, 80%, 90%, or 95% sequence identity). In cases where the segment at the 5' end is identical or similar, the resulting extension products may share identical or substantially similar sequences at the 5' ends.

In cases where multiple genes are targeted in the extension reaction, extension products of various genes will share common 5' ends. Such primer design can offer certain advantages in multiplex detection of multiple genes (e.g., at least two genes). In some cases, extension primers comprising identical or substantially similar segments at a 5' end can minimize the formation of undesirable, non-specific or side amplification products such as primer-dimer products. For example, a primer-dimer product can comprise the primer 5' end sequence and the reverse complement of that sequence at its 3' end. As a result of sequence complementarity, the 5' end of the primer dimer product can base pair with its own 3' end, thereby forming a stem loop or hair pin structure. In some cases, the stem loop structure is a stable structure that prevents additional primers from hybridizing to the primer dimer product and thus prevents the primer dimer product from participating in further amplification. In some cases, this results in the improved amplification and downstream processing of desired target sequences. Minimizing the formation of products resulting from non-specific or side amplification reactions resulting from the use of a combination of extension primers for multiple target sequences can offer advantages in addition to improved yields and efficiencies. The extension products of multiple tagged fragments (e.g., having different sequences, e.g., gene specific sequences), in some cases, can be amplified and processed in parallel (e.g., high-throughput) by relying on the shared end sequences.

The extension reaction, as will be further described elsewhere herein, can involve changes in temperature (thermocycling) or a constant temperature (isothermal). A given extension product can comprise (i) a sequence of the given tagged fragment and a complement of an extension primer sequence, or (ii) a complement of the given tagged fragment sequence and the extension primer sequence.

The extension products can then be amplified to yield amplification products. The extension products can be amplified using a primer pair comprising a first primer and a second primer. In some cases, the first primer includes the transposon sequence or a portion thereof. The first and/or second primer can include additional sequence elements useful for further polynucleotide processing steps. The second primer can include the sequence of the segment at the 5' end of the extension primer or a portion thereof. For example, the 5' end of the extension primer contains a primer binding sequence and the second primer is a primer hybridizable to the primer binding sequence. In some cases, the first primer and/or the second primer comprise additional sequences. These additional sequences can be located in any suitable region of the primer. For example, the additional sequences can include a barcode sequence (e.g., i5, i7), an amplification primer binding sequence, a sequencing primer binding sequence (e.g., Read1, Read2), or combinations thereof.

In some cases, individual amplification products can comprise a single transposon sequence or a complement thereof. In some cases, the single transposon sequence is at the 5' end of the polynucleotide. In some cases, the amplification reaction can use a Hot-start enzyme, such as a Hot-start polymerase for generating amplification products.

Amplification products of any of a variety of target polynucleotides can be generated using methods described herein. In some embodiments, the target polynucleotide is a cell-free polynucleotide. In some embodiments, the cell-free polynucleotide is cell-free DNA (cfDNA) or cell-free RNA (cfRNA). For example, a cell-free polynucleotide can be circulating tumor DNA, circulating tumor RNA, circulating fetal DNA, or circulating fetal RNA. In some embodiments, the target polynucleotide can be a genomic polynucleotide. In some cases, the genomic polynucleotide can comprise genomic DNA, genomic RNA or a mixture of genomic DNA and genomic RNA. In some cases, the genomic polynucleotide can exhibit high integrity, such as high molecular weight polynucleotides. In some cases, the genomic polynucleotide can be further bound to proteins, such as histones. In some cases, the genomic polynucleotide can be fragmented. In some cases, the polynucleotide can be methylated, such as 5-methylcytosine (e.g., partially or completely). In some cases, the polynucleotide can be unmethylated.

The polynucleotide can be extracted from a polynucleotide sample. In some cases, the polynucleotides can be obtained from intact cells or tissues. In some cases, the polynucleotides can be obtained from bodily fluids, such as blood, saliva, urine, amniotic fluid, plasma, mucous, cerebral spinal fluid, tears, synovial fluid, lymph, lactal duct fluid, and semen, etc. In certain embodiments, the polynucleotides are isolated from fresh tissues. In other cases, the polynucleotide sample can be isolated from frozen tissues. In yet other cases, the polynucleotide sample can be isolated from fixed tissues, such as formalin-fixed paraffin-embedded (FFPE) tissues. Further examples of sources of polynucleotide samples include, but are not limited to, cells dissociated from tissues, blood cells, bacteria, virus, mitochondria, chloroplast, in vitro assembled protein DNA complexes, and neutrophil extracellular traps. In some cases, the polynucleotide can be obtained from a culture of cells, e.g., a cell line. The polynucleotide can be fragmented to yield fragments suitable for downstream assays.

Figure 1B:
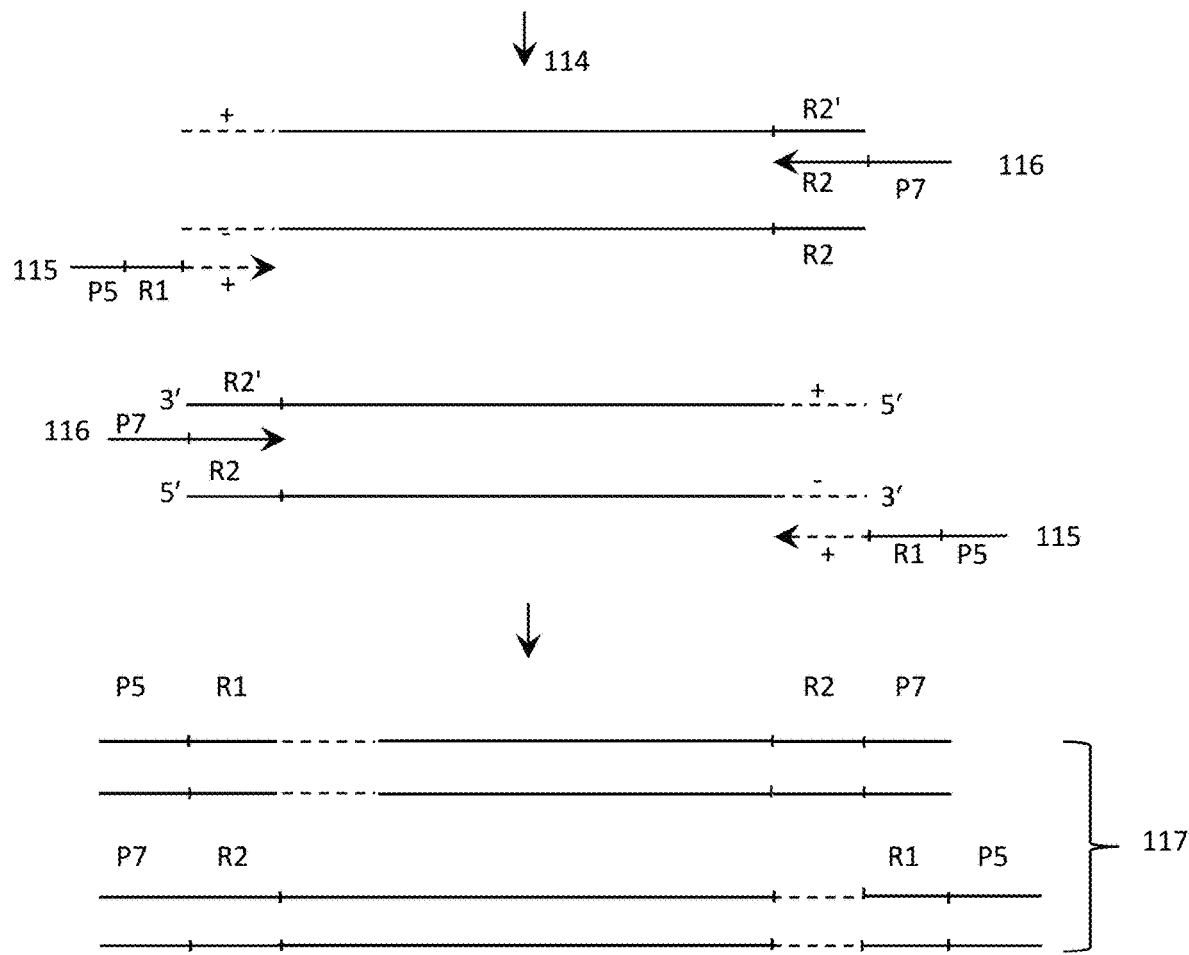

An illustrative method of forming amplification products of a polynucleotide is shown in FIGS. 1A and 1B. A double-stranded polynucleotide 101 from a polynucleotide sample comprises two complementary strands 102 and 103. Tagged fragments are formed by contacting transposomes 104 with the double-stranded polynucleotide 101. An individual transposome 104 is a homodimer comprising two monomers; each monomer includes a transposase 105 complexed with a transposon sequence. The transposon sequence is a double-stranded polynucleotide with two complementary strands 106 (+ strand) and 107 (− strand). The transposome 104 joins a strand (106, e.g., transferred strand) of the transposon sequence to a 5' end of a fragment of the polynucleotide to yield tagged fragments 108. In some cases, two transposases can contact the same target polynucleotide, resulting in a double-stranded fragment joined to transposon sequences on both strands. The tagged fragments 108 are subjected to an extension reaction 109 using an extension primer or extension primers (110 and 111) to yield extension products comprising the target sequence. Individual extension primers include a segment at a 3' end and a segment at a 5' end. The segment at the 3' end can exhibit sequence complementarity to a tagged fragment, for example, sequence complementarity to the target sequence such as a gene-specific sequence (e.g., GSP1 and GSP2). The segment at the 5' end of the extension primer pair can lack sequence complementarity to the tagged fragment. The 5' end can include sequences that are desired to be attached to the fragments, (e.g. Read2 or R2). In certain embodiments, the 5' end of all extension primers used for generating extension products are identical or share a region identical in sequence. Products resulting from primer dimer formation can form stem loop structures as a result of sequence complementarity. The extension primers are designed such that the primer dimer products, in general, form a stem loop structure 112 that are excluded from subsequent reactions. The extension products 113 subjected to an amplification reaction 114 using a primer pair. The primer pair comprises a first primer 115 and a second primer 116. The first primer comprises the transposon sequence and the second primer comprises the sequence of the segment at the 5' end of the extension primer (e.g., R2). The first primer 115 and second primer 116 can include additional sequences, such as sequencing primer binding sequences (e.g., Read1 or R1) and flow cell binding sequences (e.g., P5, P7). The amplification products 117 include tagged fragments that are flanked by, e.g., flow cell binding sequences and, e.g., sequencing primer binding sequences.

Figure 2:
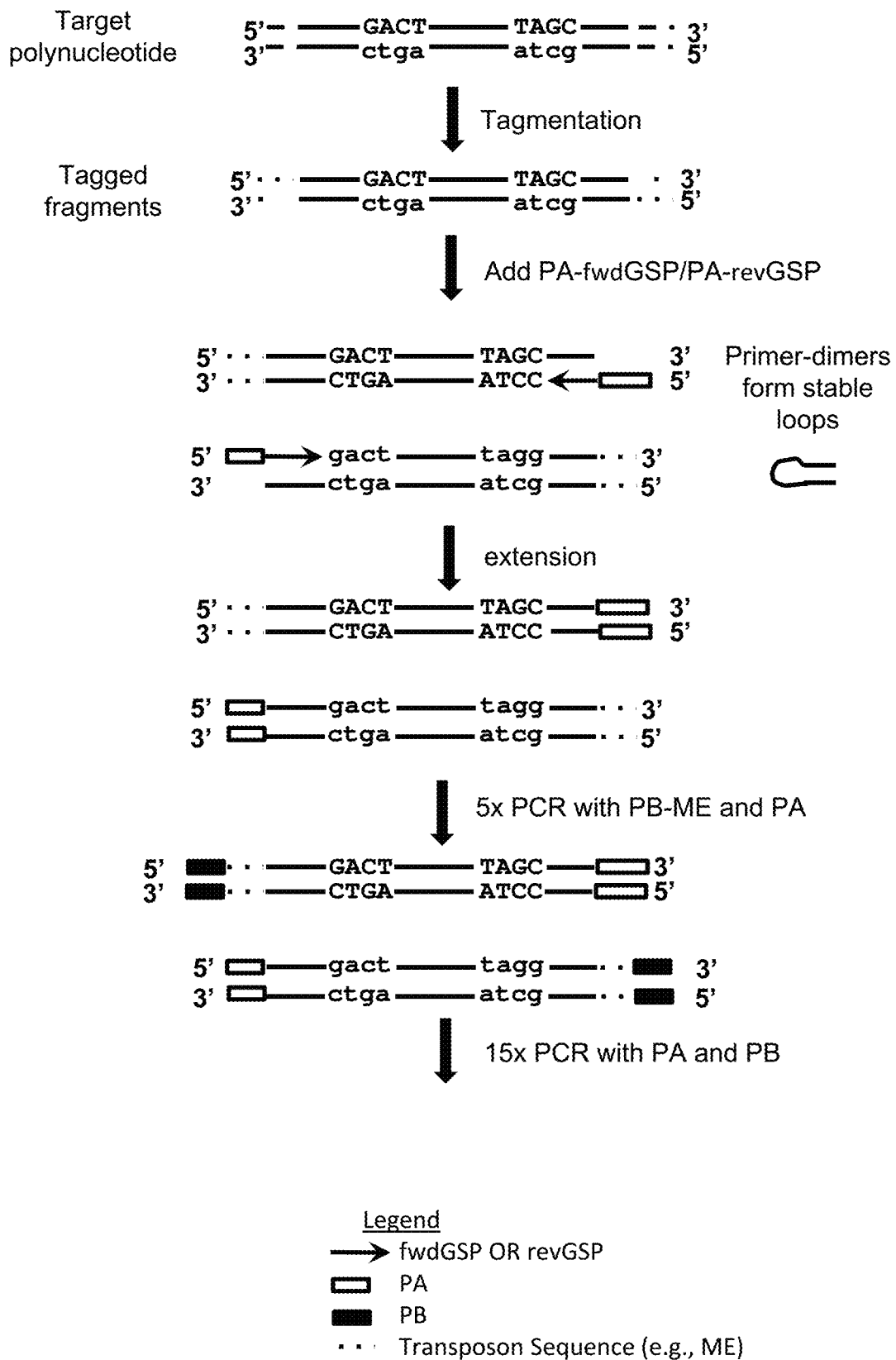
FIG. 2 illustrates an exemplary embodiment of forming amplification products.
Figure 3:
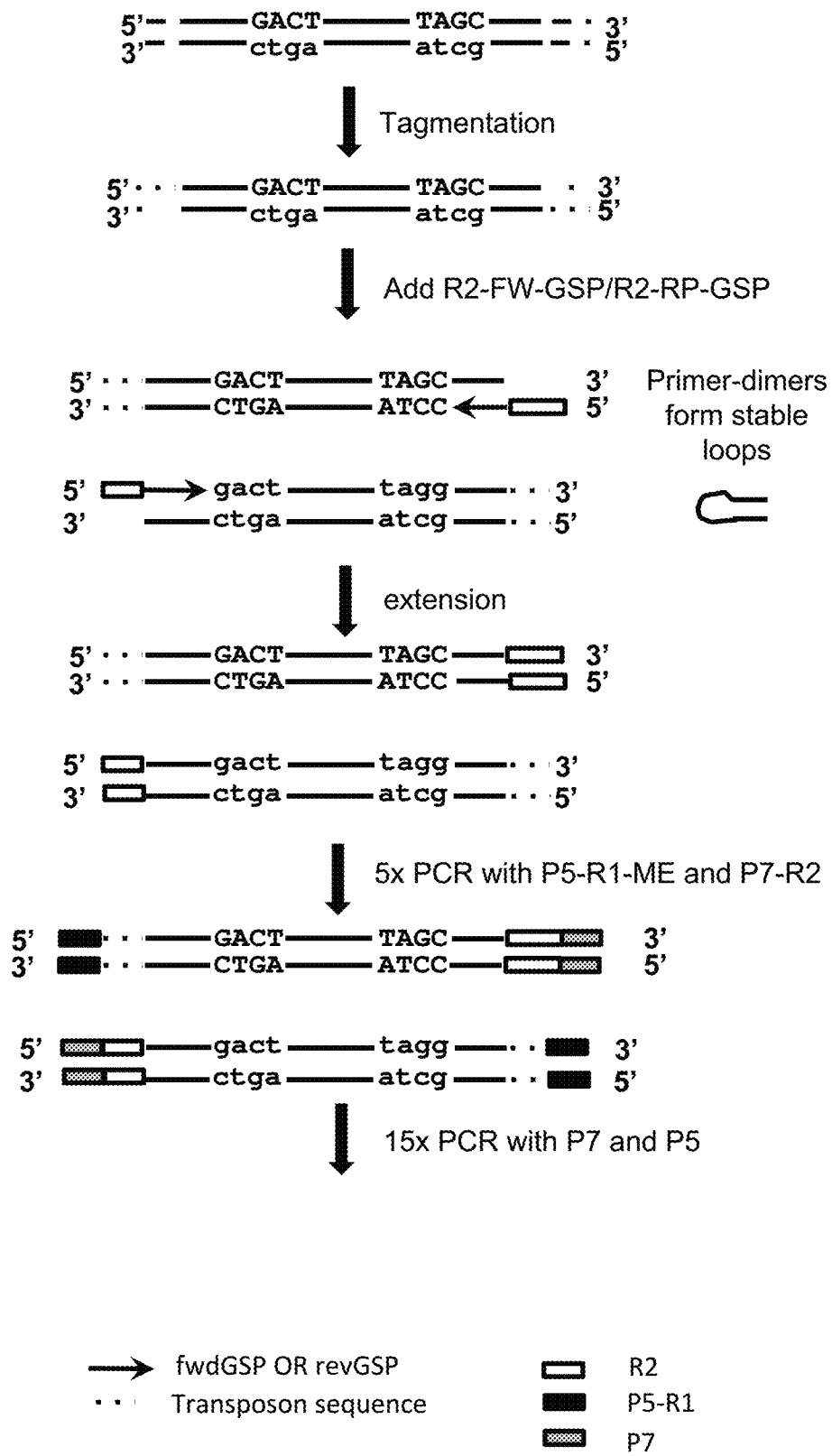
FIG. 3 illustrates an exemplary embodiment of forming amplification products.

Another illustrative method of forming amplification products is shown in FIGS. 2 and 3. In this example, the polynucleotides in a sample (e.g., cfDNA sample) are contacted with transposomes (e.g., tagmentation) to yield tagged fragments. As described previously, a tagged fragment comprises a transposon sequence joined to the 5' end of a fragment of a target polynucleotide. Subsequent to tagmentation, the non-transferred strand of the transposon sequence can be hybridized to the transferred strand. Prior to the extension reaction, the transferred strand may be separated from the non-transferred strand. The extension reaction can be effected by a hot-start polymerase (e.g., hot-start high fidelity PCR polymerase). During the initial incubation to activate the hot-start polymerase, the non-transferred strand of the transposon sequence can dissociate from the transposon. In such cases, a second transposon sequence is not incorporated into the extension product and subsequent amplification products thereof. The tagged fragments are subjected to an extension reaction using extension primers (e.g., PA-fwdGSP and/or PArevGSP, FIG. 2; R2-FW-GSP and/or R2-RP-GSP, FIG. 3) to select for tagged fragments of target gene(s). Extension primers, as described elsewhere herein, can comprise a segment at a 3' end (e.g., gene specific primer, GSP) and a segment at a 5' end (e.g., PA, R2). The segment at the 5' end of extension primers can be identical or substantially similar. Resulting primer-dimer products can form a stem loop structure as previously described. The primer dimers can be excluded from subsequent reactions, such as amplification reaction, if primers are unable to hybridize to the primer dimer product.

In some cases, the target polynucleotide comprises methylated nucleotides, for example methylated cytosines. In cases where amplification products of methylated polynucleotides are desired, for example in the study of methylation patterns or methylated sequences, the extension primers can comprise methylated bases (e.g., methylated cytosines). In cases where a target polynucleotide comprises methylated nucleotides, extension products resulting from extension reactions can comprise hemi-methylated double-stranded DNA (dsDNA). The original template (e.g., parent strand) of the extension product is methylated and the complementary strand is unmethylated. The hemi-methylated dsDNA can be fully-methylated by subjecting the extension products to a methylation reaction. In some cases, the methylation reaction can preferentially act on the hemi-methylated dsDNA. The methylation reaction can add methyl groups to the unmethylated strand based on the methylation pattern of the methylated strand.

In some cases, the methylation reaction also results in methylated primer-dimer product. As described previously, in cases where the 5' ends of extension primers are identical, the primer-dimer may preferentially form stem-loop structures. Prior to forming the stem-loop structures, primer-dimer product may be subjected to methylation to preserve the methylation pattern of the primer. Preserving cytosine methylation in primer dimer product can help stabilize the stem-loop structures during subsequent sample processing steps, for example in downstream cytosine deamination.

In some cases, the methylation reaction is catalyzed by a methyl transferase enzyme. In some cases, the methyl transferase can be a DNA methyltransferase enzyme. Non-limiting examples of the methyl transferases that can be used in methods herein include DNA (cytosine-5)-methyltransferase 1 (DNMT1), DNMT3A, and DNMT3B.

Following methylation, the extension products can be subjected to cytosine deamination. Various methods are available for effecting deamination, e.g., cytosine deamination. In some cases, cytosine deamination is effected by chemical treatment, such as bisulfate treatment. In some cases, cytosine deamination can be effected by an enzyme, such as cytidine deaminase. In some cases, cytidine deaminases such as apolipoprotein B mRNA editing enzyme, catalytic polypeptide-like (APOBEC) can be used. Non-limiting examples of APOBEC family proteins include APOBEC1, APOBEC2, APOBEC3A, APOBEC3B, APOBEC3C, APOBEC3D, APOBEC3F, APOBEC3G, APOBEC3H, APOBEC4, and Activation-induced (cytidine) deaminase. The extension products of fully-methylated dsDNA can be subjected to cytosine deamination or cytidine deamination to convert unmethylated cytosines to uracils. Methylation patterns can be later analyzed by comparing the sequences obtained, for example, from sequencing amplification products to a reference sequence and identifying single nucleotide polymorphisms (cytosines and thymidine) resulting from cytosine or cytidine deamination (e.g., bisulfite conversion or APOBEC treatment).

Figure 4:
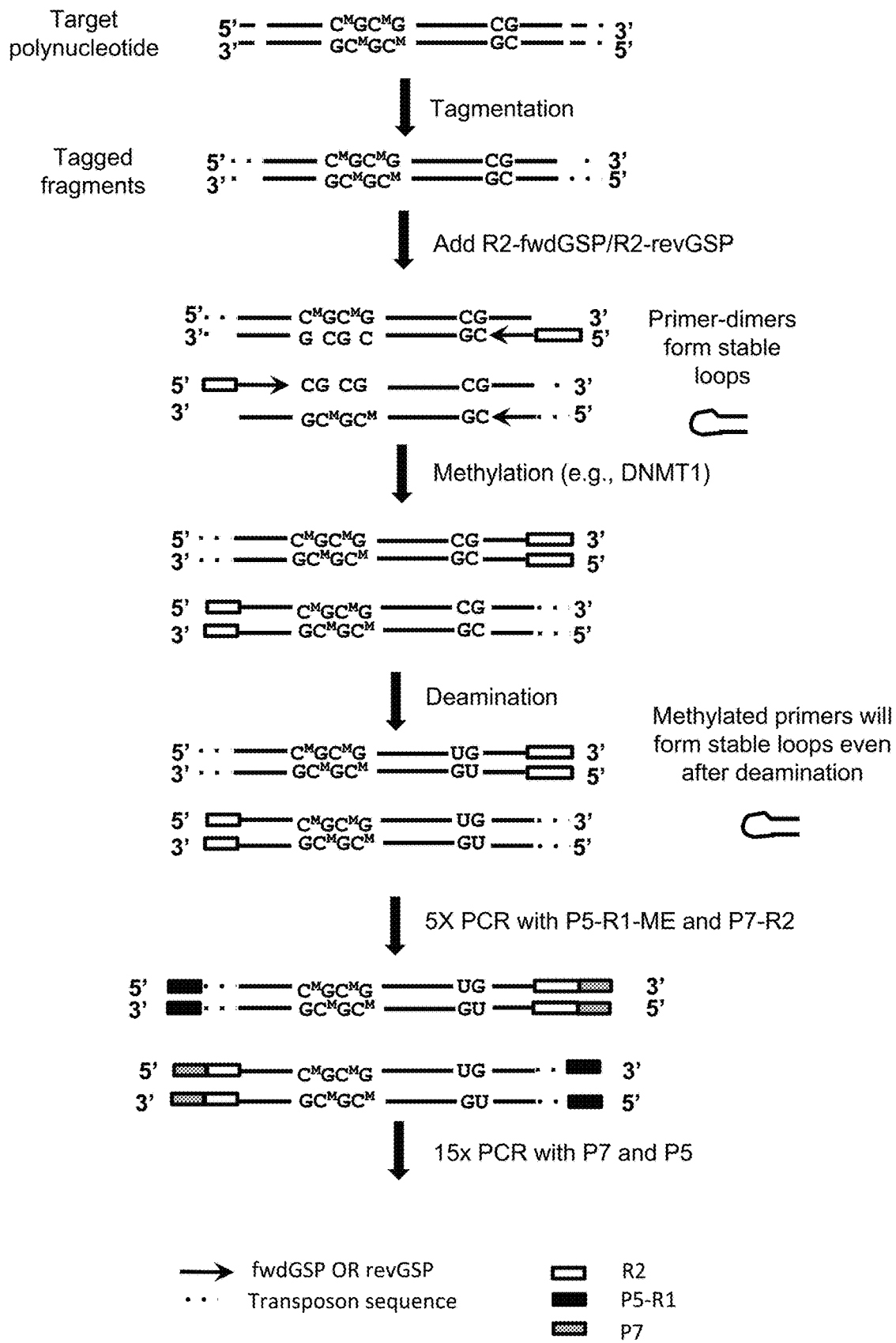
FIG. 4 illustrates an exemplary embodiment of forming amplification products of a polynucleotide having methylated nucleotides.

An illustrative method of forming amplification products of a polynucleotide comprising methylated nucleotides is shown in FIG. 4. In this example, a target polynucleotide is contacted with transposomes comprising methylated transposon sequences (e.g., cytosine methylated). Tagged fragments in which transposon sequences are joined to the 5' ends of fragments of the target polynucleotide are generated. The tagged fragments are then subjected to an extension reaction using extension primers with gene-specific sequence(s) (e.g., fwdGSP or revGSP) to select for target gene(s). The extension primer can comprise methylated nucleotides, such as methylated cytosines. The segment at the 5' end of extension primers (e.g., R2) lacks sequence complementarity to the tagged fragment. In cases where extension primers having multiple sequences are used (e.g., forward and reverse, or for multiple gene sequences), resulting non-specific products (e.g., primer-dimer product) can form a stem loop structure due to sequence complementarity at the polynucleotide ends. The primer dimers can be excluded from subsequent reactions, such as downstream amplification reactions. The extension reaction can be effected by a hot-start polymerase (e.g., hot-start high fidelity PCR polymerase). During the initial incubation to activate the hot-start polymerase, the non-transferred strand of the transposon sequence can dissociate from the transferred strand. In such cases, a second copy of a transposon sequence is not incorporated into the extension product and subsequent amplification products thereof. The resulting extension products can include transposon sequences on 5' ends of the polynucleotides and additional sequences (e.g. PA) on 3' ends. Some extension products may comprise the reverse complement of a transposon sequence at a 3' end. In some cases, the extension products are hemi-methylated since the original template (e.g., parent strand) of the extension product is methylated and the complementary strand is unmethylated. The hemi-methylated dsDNA can be fully-methylated by subjecting the extension products to a methylation reaction (e.g., using a methyl transferase such as DNMT1). In some cases, the methyl groups are added to the unmethylated strand based on the methylation pattern of the methylated strand. The extension products comprising fully-methylated dsDNA can then be subjected to cytosine deamination to convert unmethylated cytosines to uracils. Methylation patterns can be later analyzed by comparing the sequences obtained, for example, from sequencing amplification products to a reference sequence and identifying single nucleotide polymorphisms (cytosines and thymidine) resulting from cytosine deamination.

In another aspect, the present disclosure provides a method of selectively amplifying a polynucleotide comprising methylated 'CG' tandems. The polynucleotide comprising methylated 'CG' tandems is present in a sample of polynucleotides having methylated and unmethylated 'CG' tandems. A 'CG' tandem, sometimes referred to as a CpG site or CG site, generally refers to a region of DNA where a cytosine nucleotide is followed by a guanine nucleotide in a linear sequence of bases. Cytosines in CpG dinucleotides can be methylated to form 5-methylcytosine. In mammals, methylating the cytosine within a gene can change its expression (e.g., epigenetics). In some cases, change in methylation patterns, such as hypermethylation of CG tandems causing loss of expression of genes, can lead to diseases such as cancer. Aberrant methylation patterns (e.g., hyper- or hypo-methylation), in some cases, can be associated with any of a variety of diseases such as, but not limited, to cancer.

In some embodiments, the method comprises: (a) contacting the sample with transposomes to yield a plurality of tagged fragments, individual transposomes comprising a transposase complexed with a transposon sequence having methylated cytosines, wherein a given tagged fragment of the plurality comprises a transposon sequence joined to the 5' end of a segment of a polynucleotide of the sample; (b) subjecting the plurality of tagged fragments to cytosine deamination to convert unmethylated cytosine residues of the plurality of tagged fragments to uracil; (c) subjecting the plurality of tagged fragments to an extension reaction using extension primers to yield extension products, individual extension primers having a segment at a 3' end exhibiting sequence complementarity to 'CG' tandems present in tagged fragments and a segment at a 5' end lacking sequence complementarity to tagged fragments, wherein the segment at the 3' end lacks sequence complementarity to 'UG' tandems present in tagged fragments resulting from cytosine deamination of unmethylated cytosine residues in (b), and wherein individual extension products comprise (i) a tagged fragment sequence and a complement of a primer sequence, or (ii) a complement of a tagged fragment sequence and a primer sequence; and (d) amplifying the extension products using a primer pair to yield amplification products, the primer pair including a first primer comprising the transposon sequence (or a portion thereof) and a second primer comprising the sequence of the segment at the 5' end of the extension primer (or a portion thereof), wherein a given amplification product comprises a single copy of a transposon sequence or a complement thereof, thereby preferentially amplifying the polynucleotide comprising methylated 'CG' tandems.

The practice of this method of selectively amplifying a polynucleotide comprising methylated 'CG' tandems can utilize any of the transposome, transposase, and transposon sequences as described herein.

In various embodiments, not all 'CG' tandems of a polynucleotide are methylated. The resulting plurality of tagged fragments formed by contacting the polynucleotide sample with transposases can comprise tagged fragments with methylated 'CG' tandems and tagged fragments with unmethylated 'CG' tandems.

In some cases, following transposition, the transposase is removed or inactivated. The transposase can be removed by any of a variety of suitable methods, including purification, or inactivated, for example via denaturation or enzymatic treatment. Removal of the transposase can be useful in minimizing inhibition of downstream reactions, such as extension reactions or amplification reactions that may use tagged fragments as templates. In some cases, a chemical treatment can be employed for removing the transposase. For example, the chemical treatment can include treating the tagged fragments with a detergent solution, such as an SDS solution. In some cases, the tagged fragments are not subjected to treatment to remove the transposase.

The plurality of tagged fragments can subsequently be subjected to cytosine deamination to convert unmethylated cytosine residues of the plurality of tagged fragments to uracil. Unmethylated 'CG' sites in a tagged fragment can be converted to 'UG' sequences whereas methylated 'CG' sites will remain as 'CG' in sequence. Any suitable method can be used for cytosine deamination. In some cases, the cytosine deamination is effected by chemical treatment, such as bisulfite treatment. In some cases, the cytosine deamination can be effected by an enzyme, such as cytidine deaminase. In some cases, cytidine deaminases such as apolipoprotein B mRNA editing enzyme, catalytic polypeptide-like (APOBEC) can be used. Non-limiting examples of APOBEC family proteins include APOBEC1, APOBEC2, APOBEC3A, APOBEC3B, APOBEC3C, APOBEC3D, APOBEC3F, APOBEC3G, APOBEC3H, APOBEC4, and Activation-induced (cytidine) deaminase. The extension products of the fully-methylated dsDNA can be subjected to cytosine deamination to convert unmethylated cytosines to uracils. Methylation patterns of 'CG' sites can be later analyzed by comparing the sequences obtained, for example, from sequencing amplification products to a reference sequence and identifying single nucleotide polymorphisms (cytosines and thymidine) resulting from cytosine deamination (e.g., bisulfite conversion).

Following deamination, the plurality of tagged fragments can then be subjected to an extension reaction using extension primers. The extension primers can have a segment at a 5' end and a segment at a 3' end. In some cases, the segment at the 3' end exhibits sequence complementarity to a tagged fragment. In some cases, the segment at the 3' end lacks sequence complementarity to the transposon sequence. Extension products comprising methylated 'CG' tandem repeat sequences can be preferentially generated by using an extension primer comprising a 3' end having sequence complementarity to 'CG' tandem repeat sequences present in tagged fragments. Regions of 'CG' tandem repeat sequences can be located in proximity to 'CG' islands.

The 3' ends of extension primers having sequence complementarity to 'CG' tandem repeat sequences are less likely to hybridize to 'UG' sequences in the same reaction as 'U' typically base pairs with 'A'. In some cases, the segment at the 3' end of individual extension primers comprises the sequence CGCGCGG, CGCGCGA, CGCGCGT, CGCGCGC, CGGCGCGG, CGGCGCGA, CGGCGCGT, CGGCGCGC, CGCGGCGG, CGCGGCGA, CGCGGCGT, CGCGGCGC, CGGCGGCGG, CGGCGGCGA, CGGCGGCGT, or CGGCGGCGC. In some cases, the segment at the 3' end of individual extension primers includes the sequence CGCGCGG. In some cases, the segment at the 5' end of the extension primer lacks sequence complementarity to tagged fragments. For example, the segment at the 5' end can include sequences for downstream analysis or polynucleotide manipulation processes, such as a sequencing primer binding sequence (e.g., Read1 or Read2), unique molecular identifiers or barcode sequences (e.g., i5) and/or flow cell binding sequences (e.g., P5).

The extension reaction can involve changes in temperature (thermocycling) or a constant temperature (isothermal). Individual extension products can comprise (i) a tagged fragment sequence and a complement of a primer sequence, or (ii) a complement of a tagged fragment sequence and a primer sequence.

The extension products can next be amplified using a primer pair to yield amplification products. In some cases, the primer pair includes a first primer and a second primer. The first primer can include the transposon sequence or a portion thereof. The second primer can include the sequence of the segment at the 5' end of the extension primer or a portion thereof. In some cases, the first primer and the second primer comprise additional sequences. For example the first and/or the second primer can include a barcode sequence (e.g., i5, i7), an amplification primer binding sequences, a sequencing primer binding sequence (e.g., Read1, Read2), or combinations thereof.

The amplification reaction can involve changes in temperature (thermocycling) or a constant temperature (isothermal). In some cases, individual amplification products can comprise a single transposon sequence or a complement thereof. In some cases, the single transposon sequence is at the 5' end of the polynucleotide. In some cases, the amplification reaction can use a Hot-start enzyme, such as a Hot-start polymerase for generating amplification products.

In some embodiments, the sample of polynucleotides with methylated and unmethylated 'CG' tandems can comprise cell-free polynucleotides, such as cell-free DNA (cfDNA) or cell-free RNA (cfRNA). For example, the sample can comprise circulating tumor DNA, circulating tumor RNA, circulating fetal DNA, or circulating fetal RNA. In some embodiments, the sample of polynucleotides with methylated and unmethylated 'CG' tandems can comprise genomic polynucleotides. In some cases, the genomic polynucleotide can comprise genomic DNA, genomic RNA or a mixture of genomic DNA and genomic RNA. In some cases, the genomic polynucleotide can exhibit high integrity, such as high molecular weight polynucleotides. In some cases, the genomic polynucleotide can be further bound to proteins, such as histones. In some cases, the genomic polynucleotide can be fragmented. In some cases, the 'CG' tandems can be associated with differentially methylated regions. In some cases, methylation can include 5-methylcytosine.

In some cases, the polynucleotides with methylated and unmethylated 'CG' tandems can be obtained from intact cells or tissues. In some embodiments, the polynucleotides with methylated and unmethylated 'CG' tandems can be obtained from a biological fluid, such as blood, saliva, urine, amniotic fluid, plasma, mucous, cerebral spinal fluid, tears, synovial fluid, lymph, lactal duct fluid, semen, etc. In certain embodiments, the polynucleotides with methylated and unmethylated 'CG' tandems can be isolated from fresh tissues. In other cases, the polynucleotides are isolated from frozen tissues. In some embodiments, the polynucleotides with methylated and unmethylated 'CG' tandems can be obtained from fixed samples, such as a formalin-fixed paraffin embedded (FFPE) sample. Further examples of polynucleotide sample sources include, but are not limited to, cells dissociated from tissues, blood cells, bacteria, virus, mitochondria, chloroplast, in vitro assembled protein DNA complexes, neutrophil extracellular traps. In some cases, the polynucleotides can be obtained from a culture of cells, e.g., a cell line. The polynucleotide can be fragmented to yield fragments suitable for downstream assays, such as a sequencing assay.

Figure 5A:
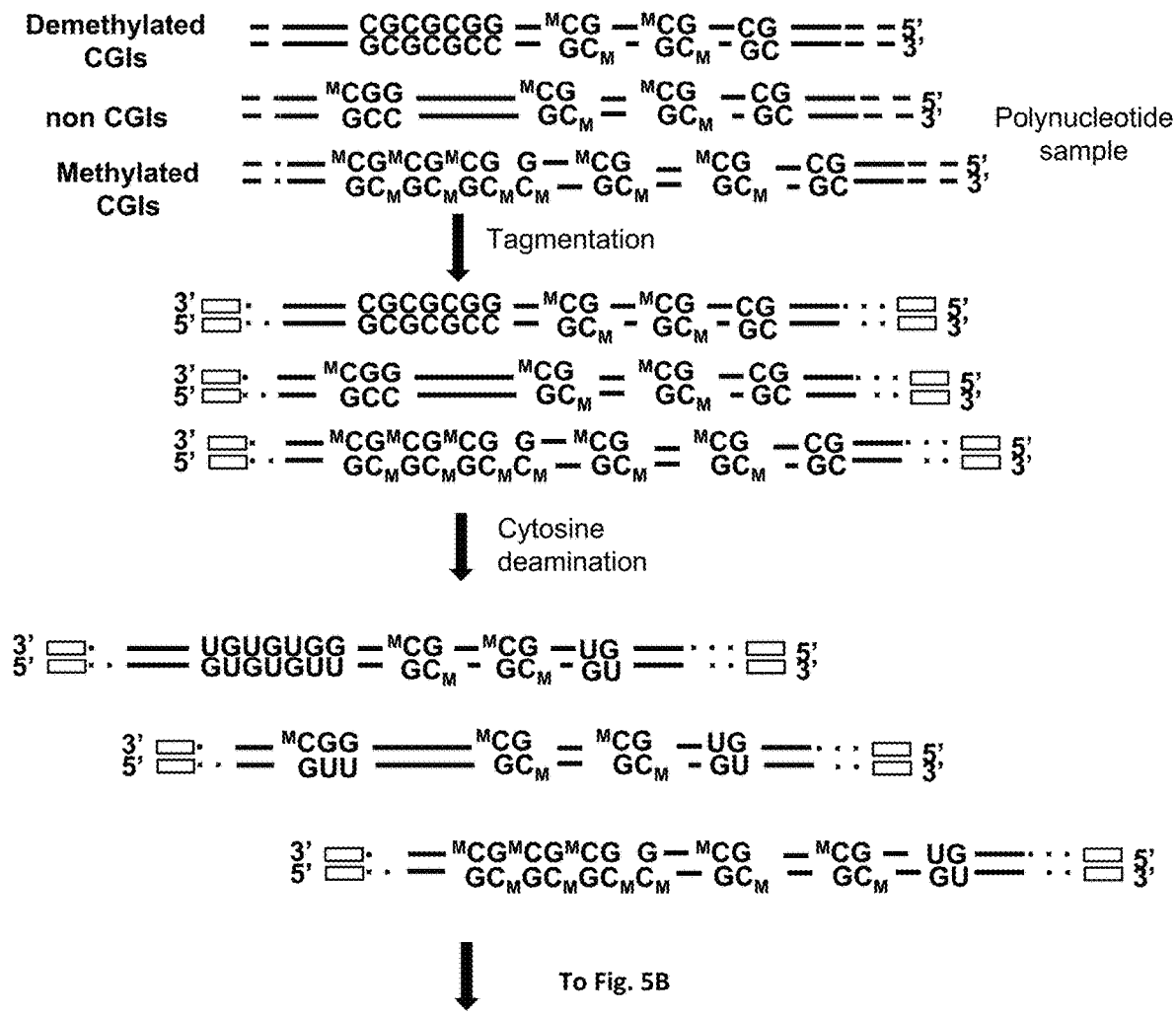
FIGS. 5A and 5B illustrate an exemplary embodiment of selectively amplifying a polynucleotide having methylated 'CG' tandems.
Figure 5B:
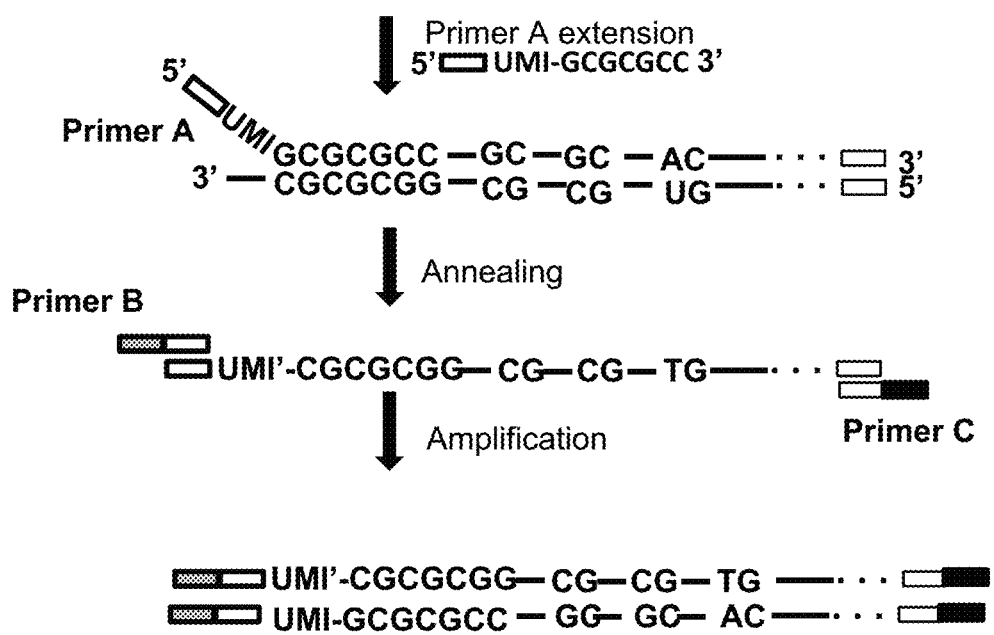

An illustrative example of a method for generating amplification products of a polynucleotide comprising methylated 'CG' tandems is shown in FIGS. 5A and 5B. In this example, a polynucleotide sample, such as cell-free DNA sample, can include polynucleotides having methylated, unmethylated and non-'CG' tandem polynucleotides (e.g., CGIs). With reference to FIG. 5A, the polynucleotides are contacted with transposomes having methylated transposon sequences (e.g., methylated cytosines). Tagged fragments in which transposons are joined to the 5' end of fragments of the polynucleotides of the sample are generated. The tagged fragments are then subjected to a cytosine deamination reaction. The deamination can be effected by treating the tagged fragments with bisulfite or APOBEC. Unmethylated cytosines in the tagged fragments can be converted to uracils while methylated cytosines remain unchanged. An extension reaction using extension primer complementary to 'CG' tandems, such as 5'-GCGCGCC-3', is used to selectively enrich tagged fragments with methylated 'CG' tandems. Following bisulfite treatment, the extension products are then subjected to an amplification reaction to yield amplification products (FIG. 5B).

In an aspect, the present disclosure provides a kit for generating extension products of a target polynucleotide. The kit can comprise one or more elements disclosed herein in relation to any of the various aspects or in any combination. In some embodiments, the kit comprises (a) a transposase; (b) a transposon sequence having a transposon element; (c) an extension primer comprising: (i) a segment at a 3' end exhibiting sequence complementarity to the target polynucleotide, and (ii) a segment at a 5' end lacking sequence complementarity to the target polynucleotide; (d) a Hot-Start polymerase; and (e) instructions for use of the kit for generating extension products from the target polynucleotide.

Contents of the kit may be contained in any suitable container. Each component may be packaged into different containers or where cross-reactivity and shelf-life permit, combinations of components can be provided in containers. Non-limiting examples of containers include a well, a plate, a tube, a chamber, a flow cell, or a chip.

The contents of the kit may be immediately usable for performing the methods described herein. In some cases, the contents of the kit are combined with other reagents in the kit or reagents supplied by a user prior to use in methods described herein. For example, a concentrated composition is diluted prior to use or a lyophilized composition is reconstituted prior to use.

A kit may provide buffers, non-limiting examples of which include sodium carbonate buffer, a sodium bicarbonate buffer, a borate buffer, a Tris buffer, a MOPS buffer, a HEPES buffer, and combinations thereof. A kit may comprise a control sample, e.g., purified DNA for use as a positive control or quantification standard.

In some embodiments, the kit further comprises a primer pair, wherein the primer pair includes a first primer comprising the transposon sequence (or a portion thereof) and a second primer comprising the sequence of the segment at the 5' end of the extension primer (or a portion thereof). In some cases, at least one of the first and second primers comprises a barcode sequence, amplification primer binding sequence, sequencing primer binding sequence, or combinations thereof.

A transposase supplied in a kit can be any transposase described herein, including, but not limited to, integrase, HERMES, or HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, any prokaryotic transposase, or any transposase related to and/or derived from those listed above. In some embodiments, the transposase supplied in the kit is a Tn transposase, an MuA transposase, or a Vibhar transposase. In some cases, the transposase supplied in the kit is a Tn transposase selected from Tn3, Tn5, Tn7, and Tn10. In some cases, the transposomes comprise a dimer of monomers, individual monomers comprising a transposase and a transposon sequence. The transposome dimer can be a homodimer or a heterodimer. In some cases, the transposition reaction can be facilitated and/or triggered by addition of one or more cations. The cations can be divalent cations such as, for example, $Ca^{2+}$, $Mg^{2+}$ and $Mn^{2+}$.

A transposon sequence supplied in a kit can be joined to a polynucleotide. A transposon sequence supplied in a kit can be a single-stranded, a double-stranded or a partially double-stranded polynucleotide sequence. In some cases, the transposon sequence can be either a double-stranded sequence or a partially double stranded sequence. A transposon sequence supplied in a kit can be completely methylated, substantially methylated, partially methylated, hemimethylated or unmethylated. In some embodiments, the transposon comprises methylated cytosines. In this case, the methylated cytosines in the transposons can remain unaffected during conversion of cytosines into uracils in a cytosine deamination reaction.

A hot-start polymerase supplied in a kit can be used for an extension reaction and/or amplification reaction. Hot-start polymerases, such as high-fidelity PCR polymerases, can be activated by incubation at an elevated temperature for sufficient length of time (e.g., 95 degrees for 1 min).

In some cases, the kit can include an SDS solution for inactivating a transposase. For example, SDS solutions with 0.1%, 0.2% or more SDS can be included in the kit.

In this case, the kit can include methyl transferase enzymes. A methyl transferase enzyme can be used for carrying out a methylation reaction. In some cases, the methyl transferase can be a DNA methyltransferase enzyme. Non-limiting examples of the methyl transferases which can be supplied in a kit provided herein include DNA (cytosine-5)-methyltransferase 1 (DNMT1), DNMT3A, and DNMT3B.

In some embodiments, the instructions for use of the kit comprise (i) contacting the target polynucleotide with a transposome to yield a tagged fragment, the transposome comprising the transposase complexed with the transposon sequence, wherein the tagged fragment comprises the transposon sequence joined to the 5' end of a segment of the target polynucleotide; (ii) subjecting the tagged fragment to an extension reaction using the extension primer to yield the extension products, wherein a given extension product comprises (i) the tagged fragment sequence and a complement of the extension primer sequence, or (ii) a complement of the tagged fragment sequence and the extension primer sequence. In some embodiments, the instructions further comprises amplifying the extension products using a primer pair to yield a plurality of amplification products, wherein individual amplification products comprise a single transposon sequence or a complement thereof.

In an aspect, the disclosure provides a reaction mixture. A reaction mixture can comprise one or more of the various components as described herein with respect to any of the various aspects and methods. In some embodiments, the disclosure provides a reaction mixture for forming extension products. The reaction mixture for forming extension products can comprise (a) a transposome comprising a transposase complexed with a transposon sequence; (b) a target polynucleotide; (c) an extension primer comprising: (i) a segment at a 3' end exhibiting sequence complementarity to the target polynucleotide, and (ii) a segment at a 5' end lacking sequence complementarity to the target polynucleotide; and (d) a Hot-Start polymerase. In some embodiments, a reaction mixture of the present disclosure is contained in a container.

As described elsewhere herein, a transposome comprising a transposase complexed with a transposon sequence, when contacted with a target polynucleotide, can yield a plurality of tagged fragments. The transposase can be any transposase disclosed herein, including, but not limited to, integrase, HERMES, or HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, any prokaryotic transposase, or any transposase related to and/or derived from those listed above. In some embodiments, the transposase of a reaction mixture is Tn transposase selected from Tn3, Tn5, Tn7, and Tn10. In some cases, the transposase cleaves the polynucleotide to produce a staggered cut that generates overhangs. The overhangs can be 1 base pair (bp), 2 bp, 3 bp, 4 bp, 5 bp, 6 bp, 7 bp, 8 bp, 9 bp, 10 bp, or more. For example, Tn5 can cleave the polynucleotide to produce 9 bp overhangs at 5' ends of the double stranded sequence. In some cases, the transposase cleave the polynucleotide to produce a blunt end cut. In some cases, the transposomes comprise a dimer of monomers, individual monomers comprising a transposase and a transposon sequence. The transposome dimer can be a homodimer or a heterodimer. In some cases, the transposition reaction can be facilitated and/or triggered by addition of one or more cations. The cations can be divalent cations such as, for example, $Ca^{2+}$, $Mg^{2+}$ and $Mn^{2+}$.

A transposon sequence of a reaction mixture, as previously discussed, can be a single-stranded, a double-stranded or a partially double-stranded polynucleotide sequence. The transposon sequence can be DNA, RNA or reverse transcribed RNA. Transposon elements recognized by transposases can also be referred as recognition sequences. Recognition sequences can include entire or any portion of the transposon sequences. Transposon elements can comprise any nucleic acid or nucleic acid analogue suitable for forming a functional complex with the transposase or integrase enzyme in a transposition reaction (e.g., in vitro or in vivo). For example, the transposon element can comprise DNA, RNA, modified bases, non-natural bases, modified backbone, and can comprise nicks in one or both strands. Transposon sequences therefore can be substantially methylated, partially methylated, hemimethylated or substantially unmethylated. In some cases, the transposon sequence can be methylated at cytosines (e.g., 5-methylcytosine). The methylated cytosines in the transposon sequence can remain unaffected during conversion of cytosines into uracils in a cytosine deamination reaction.

The target polynucleotide of a reaction mixture can be a cell-free polynucleotide. In some embodiments, the cell-free polynucleotide is cell-free DNA (cfDNA) or cell-free RNA (cfRNA). For example, a cell-free polynucleotide can be circulating tumor DNA, circulating tumor RNA, circulating fetal DNA, or circulating fetal RNA. In some embodiments, the target polynucleotide can be a genomic polynucleotide. In some cases, the target polynucleotide can be methylated, such as 5-methylcytosine. In some cases, the target polynucleotide can be unmethylated.

The target polynucleotide can be obtained from any suitable polynucleotide source. In some cases, the polynucleotide can be obtained from intact cells or tissues. In some cases, the target polynucleotide can be obtained from a biological fluid such as bodily fluids (e.g., blood, saliva, urine, amniotic fluid, plasma, mucous, cerebral spinal fluid, tears, synovial fluid, lymph, lactal duct fluid, and semen, etc.). In certain embodiments, target polynucleotides can be obtained from a fresh tissue. In other cases, target polynucleotides can be obtained from a frozen tissue. In some embodiments, target polynucleotides can be obtained from a formalin-fixed paraffin embedded (FFPE) tissue sample. Further examples of polynucleotide sources include, but are not limited to, cells dissociated from tissues, blood cells, bacteria, virus, mitochondria, chloroplast, in vitro assembled protein DNA complexes, neutrophil extracellular traps. In some cases, the target polynucleotide can be obtained from a culture of cells, e.g., a cell line. The polynucleotide can be fragmented to yield fragments suitable for downstream assays.

In some embodiments, the reaction mixture further comprises a primer pair. The primer pair can include a first primer and a second primer. In some cases, the first primer can include the transposon sequence (or a portion thereof). In some cases, the second primer can include the sequence of the segment at the 5' end of the extension primer (or a portion thereof). In some cases, at least one of the first and second primers includes additional sequences such as at least one of a barcode sequence, amplification primer binding sequence, sequencing primer binding sequence, or combinations thereof.

In an aspect, the present disclosure provides a system for performing methods disclosed herein. The system can comprise (a) a computer configured to receive a user request to perform a nucleic acid detection reaction on a polynucleotide sample; (b) one or more processors configured to execute commands that effect an amplification unit to perform a nucleic acid amplification reaction on the sample or a portion thereof in response to the user request, wherein the amplification reaction comprises the steps of: (i) contacting the polynucleotide sample with transposomes to yield a plurality of tagged fragments, individual transposomes comprising a transposase complexed with a transposon sequence, wherein a given tagged fragment of the plurality comprises a transposon sequence joined to the 5' end of a segment of a given polynucleotide of the polynucleotide sample; (ii) subjecting the plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, and wherein a given extension product comprises (i) a tagged fragment sequence and a complement of a primer sequence, or (ii) a complement of a tagged fragment sequence and a primer sequence; and (iii) amplifying the extension products using a primer pair to yield amplification products comprising a single transposon sequence or a complement thereof, wherein the primer pair includes a first primer comprising the transposon sequence (or a portion thereof) and a second primer comprising the sequence of the segment at the 5' end of the extension primer (or a portion thereof).

In some embodiments, the computer comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to design primers for amplifying a specified target sequence (which may also be provided by the customer). The computer may receive the customer request directly (e.g. by way of an input device such as a keyboard, mouse, or touch screen operated by the customer or a user entering a customer request) or indirectly (e.g. through a wired or wireless connection, including over the internet).

In some embodiments, the system comprises a report generator that sends a report to a recipient, wherein the report contains sequences of the at least two primers. The report generator may send a report automatically in response to the customer request. Alternatively, the report generator may send a report in response to instructions from an operator. The report may be transmitted to a recipient at a local or remote location using any suitable communication medium. For example, the communication medium can be a network connection, a wireless connection, or an internet connection. A report can be transmitted over such networks or connections (or any other suitable means for transmitting information, including but not limited to mailing a physical report, such as a print-out) for reception and/or for review by a recipient. The recipient can be but is not limited to the customer, or electronic system (e.g. one or more computers, and/or one or more servers). In some embodiments, the report generator sends the report to a recipient's device, such as a personal computer, phone, tablet, or other device. The report may be viewed online, saved on the recipient's device, or printed.

In one aspect, the disclosure provides a computer-readable medium comprising codes that, upon execution by one or more processors, implements a method according to any of the methods disclosed herein. Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the extension reaction and/or amplification reaction, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

In various embodiments of the aspects herein, a transposome comprises a transposase complexed with a transposon sequence. The transposase can be any naturally occurring transposase or an engineered (e.g., mutated or mutant transposase). Transposases, as previously described, refer to enzymes capable of complexing with at least one transposon sequence and catalyzing insertion or transposition of the transposon sequence into a target polynucleotide. Transposases can be of prokaryotic or eukaryotic origin.

Exemplary transposases include, but are not limited to, integrases, HERMES, and HIV integrases. Non-limiting examples of transposases include Tn transposases (e.g. Tn3, Tn5, Tn7, Tn10, Tn552, Tn903), MuA transposases, Vibhar transposases (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, Tyl, or any transposase related to and/or derived from those disclosed herein. In various embodiments of the aspects herein, the transposase of a transposome is a Tn transposase, an MuA transposase, or a Vibhar transposase. In some cases, the transposase is a Tn transposase, for example, a transposase selected from Tn3, Tn5, Tn7, and Tn10. In some embodiments, the transposase is Tn5 or a variant thereof. In some cases, the transposomes comprise a dimer of monomers comprising a transposase and a transposon sequence. The transposome dimer can be a homodimer or a heterodimer. In some cases, the transposition reaction can be facilitated and/or triggered by addition of one or more cations. The cations can be divalent cations such as, for example, $Ca^{2+}$, $Mg^{2+}$ and $Mn^{2+}$.

In some cases, the engineered transposase can have different properties relative to the parent transposase from which it was derived. In some cases, the transposase is a hyperactive transposase. In some cases, the engineered transposase can be capable of binding polynucleotides comprising modified nucleotides or nucleotide analogs. A transposase of the disclosure, for example, can be an engineered transposase which binds to any polynucleotide sequence in an unbiased manner. In some cases, a transposase of the disclosure is an engineered or mutant transposase comprising a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence identity to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. An engineered or mutant transposase of the disclosure may have increased transposition activity compared to the parent transposase. In some cases, the engineered or mutant transposase has at least about 5%, 10%, 15%, 20%, 25%, 30%, 35%, 40%, 45%, or 50% greater activity than the parent transposase. An engineered or mutant transposase of the disclosure may have decreased transposition activity compared to the parent transposase. In some cases, an engineered or mutant transposase has at least about 5%, 10%, 15%, 20%, 25%, 30%, 35%, 40%, 45%, or 50% lower activity than the parent transposase.

In various embodiments of the aspects herein, transposon sequences can be DNA, RNA or reverse transcribed RNA (e.g., cDNA). A transposon element of a transposon sequence can be recognized by transposases and can be referred to as a recognition sequence. Recognition sequences can include the entire transposon sequence or any portion thereof. In some cases, either both ends or a single end of the transposon sequence can be recognized by a transposase. For example, Tn5 transposase can recognize a 19 bp sequence on either end of the transposon sequence.

In some cases, a transposon sequence can join to a polynucleotide in a sequence-dependent manner. For example, transposons Passport, Himar1, Hsmar1, Frog Prince, and Sleeping Beauty may preferentially join to polynucleotide sequences enriched in 'TA'. Similarly, transposons PiggyBac and PiggyBat may preferentially join to the polynucleotide sequences enriched in 'TTAA'. In some cases, a transposon sequence can join to polynucleotide sequences in a sequence-independent manner. For example, transposons Tol2 and TcBuster can join to any polynucleotide sequences that are 8 bp long. Transposons can be substantially methylated, partially methylated, hemimethylated or substantially unmethylated. As described elsewhere herein, transposon sequences can comprise methylated cytosines when downstream sample preparation steps include cytosine deamination.

In various embodiments of the aspects herein, a polynucleotide or a target polynucleotide comprises a cell-free polynucleotide, including but not limited to a cell-free DNA or RNA (cfDNA or cfRNA). In some embodiments, a cell-free polynucleotide is a circulating tumor DNA or RNA (ctDNA or ctRNA). In some embodiments, a cell-free polynucleotide comprises fetal DNA or RNA.

Cell-free polynucleotides include polynucleotides originating from a cell but not directly obtained from a cellular source, such as a tissue sample. Non-limiting examples of sources from which cell-free polynucleotides may originate are normal cells and tissue, abnormal cells and tissue (e.g., diseased cells or tissue, e.g., cancerous cells or tissue), fetal cells and tissue, and pathogens. A cell-free polynucleotide present in a non-cellular source can result from cell death (e.g., apoptosis or necrosis) or cell shedding. Sequence analysis of cell-free polynucleotides can be used to characterize the cell or population of cells from which the cell-free polynucleotide is derived, such as tumor cells (e.g., in cancer detection), fetal cells (e.g., in prenatal diagnostics), cells from transplanted tissue (e.g., in early detection of transplant failure), or a pathogen (e.g., bacteria or virus).

Any cell free polynucleotide can be used by embodiments of the present disclosure. Cell free polynucleotides can be obtained from a subject, such as any animal or living organism. Non-limiting examples of subjects are mammals, such as humans, non-human primates, rodents such as mice and rats, dogs, cats, pigs, sheep, rabbits and others. In some embodiments, a subject is healthy, and cell-free polynucleotides obtained from the subject may not comprise a sequence variant associated with a disease or disorder. In some embodiments, a subject is suspected of having a disease or disorder, and cell-free polynucleotides obtained from the subject may comprise a sequence variant associated with the disease or disorder. In some embodiments, a subject is pregnant, and cell-free polynucleotides obtained from the subject comprise fetal polynucleotides.

Cell-free polynucleotides can be obtained from various non-cellular sources. Non-limiting examples of non-cellular sources from which cell-free polynucleotides can be obtained are serum, plasma, blood, perspiration, saliva, urine, stool, semen, mucosal excretions, spinal fluid, amniotic fluid, and lymph fluid. Various methods for collecting samples of non-cellular sources from which cell-free polynucleotides can be obtained are available. In some embodiments, samples of non-cellular sources from which cell-free polynucleotides can be obtained are from a subject. In some embodiments, samples are obtained by venipuncture. In some embodiments, samples are obtained by aspiration.

Various methods and commercial kits are available for obtaining cell-free polynucleotides, such as cell-free DNA or RNA, from a sample. Examples of methods and kits for extracting and isolating cell-free polynucleotides, including cell-free DNA, are phenol/chloroform extraction, phenol/chloroform/isoamyl alcohol (PCI)-glycogen extraction, NaI (sodium iodide) extraction, guanidine-resin extraction, the QIAmp DNA Blood Midi kit with carrier RNA, the ChargeSwitch serum kit, the ZR serum DNA kit, Qiagen Qubit™ dsDNA HS Assay kit, Agilent™ DNA 1000 kit, TruSeq™ Sequencing Library Preparation, and the Puregene DNA purification system Blood Kit.

Cell-free polynucleotides, including cell-free DNA and RNA, can be extracted and isolated from bodily fluids through a partitioning step in which cell-free polynucleotides are separated from cells and other non-soluble components of the bodily fluid. Examples of partitioning techniques are centrifugation and filtration. In some embodiments, cells are not partitioned from cell-free polynucleotides first, but rather lysed. In some embodiments, the genomic DNA of intact cells is partitioned through selective precipitation. Cell-free polynucleotides, including DNA, may remain soluble and may be separated from insoluble genomic DNA and extracted. According to some procedures, after addition of buffers and other wash steps specific to different kits, DNA may be precipitated using isopropanol precipitation. Further clean up steps may be used such as silica based columns to remove contaminants or salts. General steps may be optimized for specific applications. Non-specific bulk carrier polynucleotides, for example, may be added throughout the reaction to optimize certain aspects of the procedure such as yield.

In some embodiments of any of the various aspects disclosed herein, a polynucleotide or a target polynucleotide comprises genomic DNA. In some embodiments, a polynucleotide or a target polynucleotide is derived from genomic DNA. Genomic DNA can be obtained from a cell or tissue sample using various methods and commercial kits available, such as a Qiagen DNeasy Tissue Kit. Genomic DNA can be obtained and purified from a sample using any extraction, isolation, and purification method previously described elsewhere herein. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). For example, nucleic acids can be isolated and purified using solid phase reversible immobilization (SPRI) beads (Agencourt AMPure XP). In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodide, Hoechst stain, SYBR gold, ethidium bromide).

In some embodiments, a polynucleotide or a target polynucleotide comprises fragmented cell-free DNA or fragmented genomic DNA. In some cases, fragmenting occurs as a result or prior sample processing steps, such as formalin fixation, paraffin embedding, or freezing. In some cases, a polynucleotide is fragmented to yield shorter fragments.

Various methods are available for fragmenting polynucleotides, including but not limited to chemical, enzymatic, and mechanical methods such as sonication, shearing, and contacting with restriction enzymes. In some embodiments, cell-free DNA fragments are approximately uniform in length. In some embodiments, cell-free DNA fragments are not approximately uniform in length. In some embodiments, cell-free DNA fragments have an average length from about 50 to about 1000 nucleotides in length. In some embodiments, cell-free DNA fragments have an average length from about 50 to about 500 nucleotides in length. In some embodiments, cell-free DNA fragments have an average length from about 50 to about 250 nucleotides in length. In some embodiments, cell-free DNA fragments have an average length from about 50 to about 200 nucleotides in length. In some embodiments, cell-free DNA fragments have an average length from about 50 to about 100 nucleotides in length. In some embodiments, cell-free DNA fragments have an average length from about 40 to about 1000 nucleotides in length. In some embodiments, cell-free DNA fragments have an average length from about 40 to about 500 nucleotides in length. In some embodiments, cell-free DNA fragments have an average length from about 40 to about 250 nucleotides in length. In some embodiments, cell-free DNA fragments have an average length from about 40 to about 200 nucleotides in length. In some embodiments, cell-free DNA fragments have an average length from about 40 to about 100 nucleotides in length.

In some embodiments, genomic DNA is fragmented into polynucleotides of shorter lengths. In some embodiments, genomic DNA fragments are approximately uniform in length. In some embodiments, genomic DNA fragments are not approximately uniform in length. In some embodiments, genomic DNA fragments have an average length from about 50 to about 100 nucleotides in length. In some embodiments, genomic DNA fragments have an average length from about 50 and 250 nucleotides in length. In some embodiments, genomic DNA fragments have an average length from about 50 and 500 nucleotides in length. In some embodiments, genomic DNA fragments have an average length from about 50 and 750 nucleotides in length. In some embodiments, genomic DNA fragments have an average length from about 100 and 1000 nucleotides in length.

In some cases, the polynucleotides can be obtained from intact cells or tissues. In some cases, the polynucleotides can be obtained from bodily fluids, such as blood, saliva, urine, amniotic fluid, plasma, mucous, cerebral spinal fluid, tears, synovial fluid, lymph, lactal duct fluid, and semen, etc. In certain embodiments, the polynucleotides are isolated from fresh tissues. In other cases, the polynucleotide sample can be isolated from frozen tissues. In yet other cases, the polynucleotide sample can be isolated from fixed tissues. Further examples of sources of polynucleotide samples include, but are not limited to, cells dissociated from tissues, blood cells, cells obtained from formalin-fixed paraffin embedded (FFPE) tissues, bacteria, virus, mitochondria, chloroplast, in vitro assembled protein DNA complexes, and neutrophil extracellular traps. In some cases, the polynucleotide can be obtained from a culture of cells, e.g., a cell line.

Some embodiments of the present disclosure comprise primer extension and amplification reactions, such as generating extension products and amplifying extension products. Primer extension reactions can involve changes in temperature (thermocycling) or a constant temperature (isothermal). In some embodiments, primer extension reactions comprise polymerase chain reaction (PCR). PCR involves cycling through multiple stages of denaturation, annealing of primer pairs to opposite strands, and primer extension to exponentially increase copy numbers of the target sequence, at least some of these stages generally occurring at different reaction temperatures. Non-limiting examples of PCR amplification techniques are quantitative PCR (qPCR or realtime PCR), reverse transcription PCR (RT-PCR), digital PCR (dPCR or dePCR), target-specific PCR, and quantitative reverse transcription PCR (qRT-PCR). Examples of polymerase enzymes that can be used for PCR are thermostable polymerases, including but not limited to, *Thermus thermophilus* HB8; mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y), Taq (G46D; F667Y; E681I), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerase enzymes that can be used for PCR are non-thermostable polymerases, including, but are not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase.

In some embodiments, primer extension and amplification reactions comprise isothermal reactions. Non-limiting examples of isothermal amplification technologies are ligase chain reaction (LCR); transcription mediated amplification (TMA); nucleic acid sequence-based amplification (NASBA); signal mediated amplification of RNA technology (SMART); strand displacement amplification (SDA); thermophilic SDA; rolling circle amplification (RCA); loop-mediated isothermal amplification of DNA (LAMP); helicase-dependent amplification (HDA); single primer isothermal amplification (SPIA); and circular helicase-dependent amplification (cHDA).

In various embodiments of the aspects herein, a hot-start polymerase is used for extension and/or amplification. The term "hot-start" generally refers to a means of limiting the availability of an essential reaction component (e.g., a polymerase) when the reaction mixture is maintained at a first temperature (typically a lower temperature) until a second temperature (typically a higher temperature) is reached which allows the essential component to participate in the reaction. Hot-start reactions typically involve incubation at a first (e.g., lower) temperature and subsequent elevation to a second (e.g., higher) temperature which allows the desired reaction to take place. Activation of the hot start reaction can be achieved by incubating a reaction mixture at a temperature which is equal to or higher than the primer hybridization (annealing) temperature. Use of a temperature which is equal to or greater than the primer hybridization temperature can ensure primer binding specificity. The length of incubation required to recover enzyme activity depends on the temperature and pH of the reaction mixture and on the stability of the enzyme. A wide range of incubation conditions are usable; optimal conditions may be determined empirically for each reaction. The solutions can be optionally heated to and held at a first temperature for a first period of time suitable for hot-start activation of the nucleic acid polymerases.

Non-limiting exemplary hot start mechanisms include, but are not limited to, antibodies or combinations of antibodies that block nucleic acid polymerase activity at lower temperatures and which dissociate from the polymerase at elevated temperatures; affibodies or combinations of affibodies, sometimes referred to as antibody mimetics; oligonucleotides that block nucleic acid polymerase activity at lower temperatures and which dissociate from the polymerase at elevated temperatures; reversible chemical modification of the nucleic acid polymerase such that the nucleic acid polymerase activity is blocked at lower temperatures and the modifications reverse or dissociate at elevated temperatures; amino acid mutations of the nucleic acid polymerase that provide reduced activity at lower temperatures; nucleic acid polymerase fusion proteins including hyperstable DNA binding domains and topoisomerases; ligands that inhibit the nucleic acid polymerase in a temperature-dependent manner; single-stranded binding proteins that sequester primers at low temperatures; thermostable pyrophosphatase which hydrolyzes inorganic pyrophosphate at elevated temperatures; thermolabile blockers, such as a polymerase blocking protein; primer competitor sequences; modified primer constructs; modified primers that improve hybridization selectivity; primers with 3' modifications that are removable by 3'-5' exonuclease activity; primers with modified nucleobases that are removable by UV irradiation; primer modifications that are removable by thermal deprotection; or modification of the dNTPs with thermolabile modification groups. Agents that are used as hot start mechanisms, such as, but not limited to, antibodies, oligonucleotides, Affibodies, chemical modifications, etc., may be referred to as "hot start inhibitors."

In some embodiments, a hot start composition comprises an antibody specific for the polymerase. In some embodiments, a hot start composition comprises an antibody specific for the polymerase, which is bound to the polymerase. In some embodiments, a hot start composition comprises an inhibitor specific for the polymerase, which is bound to the polymerase. In some embodiments, the inhibitor comprises an Affibody. In some embodiments, the inhibitor comprises an oligonucleotide. In some embodiments, the inhibitor comprises a chemical modification. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MTDSCI; Minerva Biolabs GmbH; New England Biolabs; Novagen; Promega; QIAGEN; Roche Applied Science; Sigma-Aldrich; Stratagene; Takara Minis Bio; USB Corp.; Yorkshire Bioscience Ltd; and the like.

In some embodiments of any of the various aspects of the present disclosure, a primer may comprise one or more portions. For example, a primer may comprise one or more amplification primer annealing sequences or complements thereof; one or more sequencing primer annealing sequences or complements thereof; one or more barcode sequences; one or more common sequences shared among multiple different primers; one or more restriction enzyme recognition sites; one or more probe binding sites or sequencing adapters (e.g., for attachment to a sequencing platform, such as a flow cell for massive parallel sequencing); one or more random or near-random sequences (e.g. one or more nucleotides selected at random from a set of two or more different nucleotides at one or more positions, with each of the different nucleotides selected at one or more positions represented in a pool of primers comprising the random sequence); and combinations thereof.

Non-limiting examples of next-generation sequencing methods are single-molecule real-time sequencing, ion semiconductor sequencing, pyrosequencing, sequencing by synthesis, sequencing by ligation, and chain termination. Sequencing adapters for flow cell attachment may comprise any suitable sequence compatible with next generation sequencing systems, e.g., 454 Sequencing, Ion Torrent Proton or PGM, and Illumina X10. Non-limiting examples of sequencing adapters for next generation sequencing methods include P5 and P7 adapters suitable for use with Illumina sequencing systems; TruSeq Universal Adapter; and TruSeq Indexed Adapter. In some embodiments, a sequencing adapter can be used to enrich, e.g., via amplification, such as polymerase chain reaction (PCR), for polynucleotides comprising the adapter sequence. Sequencing adapters can further comprise a barcode sequence and/or a sample index sequence.

In some embodiments, a primer comprises a barcode sequence. A barcode sequence refers to a known nucleic acid sequence that allows some feature of a polynucleotide with which the barcode is associated to be identified. Barcodes can each have a length within a range of 5 to 35 nucleotides, 6 to 30 nucleotides, or 8 to 20 nucleotides. In some embodiments, barcodes are at least 3, 4, 5, 6, 7, 8, 9, 10, 11, 12, 13, 14, or 15 nucleotides in length. In some embodiments, barcodes are less than 6 nucleotides in length. In some embodiments, barcodes associated with some target polynucleotides may be a different length than barcodes associated with other target polynucleotides. The melting temperatures of barcodes within a set can be within ±10° C. of one another, within ±5° C. of one another, or within ±2° C. of one another. Barcodes can be members of a minimally cross-hybridizing set. For example, the nucleotide sequence of each member of such a set can be sufficiently different from that of every other member of the set that no member can form a stable duplex with the complement of any other member under moderate or stringent hybridization conditions. The nucleotide sequence of each member of a minimally cross-hybridizing set can differ from those of every other member by at least two nucleotides. Some barcode technologies are described in Winzeler et al. (1999) Science 285:901; Brenner (2000) Genome Biol. 1: 1 Kumar et al. (2001) Nature Rev. 2:302; Giaever et al. (2004) Proc. Natl. Acad. Sci. USA 101: 793; Eason et al. (2004) Proc. Natl. Acad. Sci. USA 101: 11046; and Brenner (2004) Genome Biol. 5:240, each of which is herein incorporated in its entirety by reference.

Amplification products (also referred to as amplicons) produced according to methods herein can be analyzed by sequencing. A variety of sequencing methodologies are available for sequencing amplification products. In some embodiments, high-throughput sequencing methodologies are used. Non-limiting examples of sequencing methodologies that can be used include sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300 nucleotides or more in length. In some embodiments, sequencing comprises a sequencing-by-synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/ polymerase complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, and then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In some embodiments, the amplification products are sequenced to detect a sequence variant, e.g., inversion, deletion, duplication, translocation, and rare somatic mutations, with respect to a reference sequence or in a background of no mutations. In some embodiments, the sequence variant is correlated with disease (e.g., cancer). In some embodiments, the sequence variant is not correlated with disease. In general, sequence variants for which there is statistical, biological, and/or functional evidence of association with a disease or trait are referred to as "causal genetic variants." A single causal genetic variant can be associated with more than one disease or trait. In some cases, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Additional non-limiting examples of causal genetic variants are described in WO2014015084. Additional non-limiting examples of methods for the identification of rare sequence variants are described in WO2015089333.

In some embodiments of any of the various aspects of the present disclosure, amplification products are purified prior to sequencing. Amplification products can be purified by various methods. Amplification products may be purified to remove excess or unwanted reagents, reactants, or products. Amplification products may further be purified by size, sequence, or other physical or chemical characteristic. In some embodiments, amplicons may be subjected to size exclusion chromatography. In some embodiments, amplification products may be subjected to fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6×binding buffer during mixing with DNA fragments may be used to preferentially bind DNA fragments larger than about 500 base pairs (bp).

Embodiments of the disclosure provided herein can be used to enrich for amplification products of tagged fragments comprising a variety of sequence variants associated with one or more kinds of cancer. Suitable target sequences of oncological significance that find use in the methods of the disclosure include, but are not limited to, alterations in the TP53 gene, the ALK gene, the KRAS gene, the PIK3CA gene, the BRAF gene, the EGFR gene, and the KIT gene. A target sequence the may be specifically amplified, and/or specifically analyzed for sequence variants may be all or part of a cancer-associated gene. In some embodiments, one or more sequence variants are identified in the TP53 gene. TP53 is one of the most frequently mutated genes in human cancers, for example, TP53 mutations are found in 45% of ovarian cancers, 43% of large intestinal cancers, and 42% of cancers of the upper aerodigestive track (see e.g. M. Olivier, et, al. TP53 Mutations in Human Cancers: Origins, Consequences, and Clinical Use. Cold Spring Harb Perspect Biol. 2010 January; 2(1). Characterization of the mutation status of TP53 can aid in clinical diagnosis, provide prognostic value, and influence treatment for cancer patients. For example, TP53 mutations may be used as a predictor of a poor prognosis for patients in CNS tumors derived from glial cells and a predictor of rapid disease progression in patients with chronic lymphocytic leukemia (see e.g. McLendon R E, et al. Cancer. 2005 Oct. 15; 1 04(8): 1693-9; Dicker F, et al. Leukemia. 2009 January; 23(1): 117-24). Sequence variation can occur anywhere within the gene. Thus, all or part of the TP53 gene can be evaluated herein. That is, as described elsewhere herein, when target specific components (e.g. target specific primers) are used, a plurality of TP53 specific sequences can be used, for example to amplify and detect fragments spanning the gene, rather than just one or more selected subsequences (such as mutation "hot spots") as may be used for selected targets. Alternatively, target-specific primers may be designed that hybridize upstream or downstream of one or more selected subsequences (such a nucleotide or nucleotide region associated with an increased rate of mutation among a class of subjects, also encompassed by the term "hot spot").

Additional non-limiting examples of genes associated with cancer, all or a portion of which may be analyzed for sequence variants according to a method described herein include, but are not limited to PTEN; ATM; ATR; EGFR; ERBB2; ERBB3; ERBB4; Notch 1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF;

IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; and Ape.

Examples of cancers with which selected gene sequences may be associated include, without limitation, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

Further understanding of the disclosure is provided through the following partial list of numbered embodiments. 1. A method of forming amplification products of a target polynucleotide, comprising: (a) contacting a target polynucleotide present in a polynucleotide sample with transposomes to yield a plurality of tagged fragments, individual transposomes comprising a transposase complexed with a transposon sequence having a transposon element, wherein a given tagged fragment of the plurality comprises a transposon sequence joined to the 5' end of a segment of the target polynucleotide; (b) subjecting said plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, wherein a given extension product comprises (i) a sequence of the given tagged fragment and a complement of an extension primer sequence, or (ii) a complement of the given tagged fragment sequence and the extension primer sequence; and (c) amplifying the extension products using a primer pair to yield amplification products, the primer pair including a first primer comprising the transposon sequence or a portion thereof and a second primer comprising the sequence of the segment at the 5' end of the extension primer or a portion thereof, wherein individual amplification products comprise a single copy of the transposon sequence or a complement thereof 2. The method of embodiment 1, wherein the segment at the 3' end of individual extension primers lacks sequence complementarity to the transposon sequence. 3. The method of any one of embodiments 1-2, wherein the segment at the 3' end of individual extension primers comprises a gene specific sequence. 4. The method of any one of embodiments 1-3, wherein the extension primers comprise a mixture of gene specific extension primers. 5. The method of any one of embodiments 1-4, wherein the extension primers share an identical segment at the 5' end. 6. The method of any one of claims 1-5, wherein the extension primers comprise methylated cytosines. 7. The method of any one of embodiments 1-6, wherein the extension products comprise hemi-methylated double-stranded DNA. 8. The method of any one of embodiments 1-7, further comprising, subsequent to (b), subjecting said extension products comprising hemi-methylated double-stranded DNA to a methylation reaction to yield extension products comprising fully methylated double-stranded DNA. 9. The method of any one of embodiments 1-8, wherein methylation is effected by methyl transferase activity. 10. The method of any one of embodiments 1-8, wherein methylation is effected by a DNA methyltransferase enzyme. 11. The method of any one of embodiments 1-10, wherein the DNA methyltransferase enzyme is DNA (cytosine-5)-methyltransferase 1 (DNMT1). 12. The method of any one of embodiments 1-11, further comprising, prior to (c), subjecting said extension products comprising fully methylated double-stranded DNA to cytosine deamination to convert unmethylated cytosines to uracil. 13. The method of any one of embodiments 1-12, wherein cytosine deamination is effected by bisulfite or apolipoprotein B mRNA editing enzyme, catalytic polypeptide-like (APOBEC). 14. The method of any one of claims 1-5, wherein at least one of the first and second primers of the primer pair comprises a barcode sequence, an amplification primer binding sequence, a sequencing primer binding sequence, or combinations thereof 15. The method of any one of claims 1-5, wherein the polynucleotide is a cell-free polynucleotide. 16. The method of any one of claims 1-5, wherein the polynucleotide is a genomic polynucleotide. 17. The method of any one of claims 1-5, wherein the polynucleotide sample is obtained from a formalin-fixed paraffin-embedded (FFPE) tissue sample. 18. The method of any one of claims 1-5, wherein the polynucleotide sample is obtained from a frozen tissue sample. 19. The method of any one of claims 1-5, wherein the polynucleotide sample is obtained from a biological fluid. 20. The method of any one of claims 1-5, wherein the transposon sequence comprises methylated cytosines. 21. The method of any one of claims 1-5, wherein the transposase is a Tn transposase, an MuA transposase, or a Vibhar transposase. 22. The method of any one of embodiments 1-21, wherein the transposase is a Tn transposase selected from Tn3, Tn5, Tn7, and Tn10. 23. The method of any one of claims 1-5, wherein individual transposomes comprise a dimer of monomers, which monomers comprise a transposase complexed with a transposon sequence. 24. The method of any one of claims 1-5, wherein the amplifying of (c) is effected by a Hot-Start enzyme. 25. The method of any one of embodiments 1-24, wherein the Hot-Start enzyme is a Hot-Start polymerase. 26. A method of selectively amplifying a polynucleotide comprising methylated 'CG' tandems, wherein the polynucleotide comprising methylated 'CG tandems is present in a sample of polynucleotides having methylated and unmethylated 'CG' tandems, comprising: (a) contacting the sample with transposomes to yield a plurality of tagged fragments, individual transposomes comprising a transposase complexed with a transposon sequence having methylated cytosines, wherein a given tagged fragment of the plurality comprises a transposon sequence joined to the 5' end of a segment of a polynucleotide of the sample; (b) subjecting said plurality of tagged fragments to cytosine deamination to convert unmethylated cytosine residues of said plurality of tagged fragments to uracil; (c) subjecting said plurality of tagged fragments to an extension reaction using extension primers to yield extension products, individual extension primers having a segment at a 3' end exhibiting sequence complementarity to 'CG' tandems present in tagged fragments and a segment at a 5' end lacking sequence complementarity to tagged fragments, wherein said segment at the 3' end lacks sequence complementarity to 'UG' tandems present in tagged fragments resulting from cytosine deamination of unmethylated cytosine residues in (b), and wherein individual extension products comprise (i) a tagged fragment sequence and a complement of a primer sequence, or (ii) a complement of a tagged fragment sequence and a primer sequence; and (d) amplifying the extension products using a primer pair to yield amplification products, the primer pair including a first primer comprising the transposon sequence or a portion thereof and a second primer comprising the sequence of the segment at the 5' end of the extension primer or a portion thereof, wherein a given amplification product comprises a single copy of the transposon sequence or a complement thereof, thereby preferentially amplifying the polynucleotide comprising methylated 'CG' tandems. 27. The method of any one of embodiments 1-26, wherein cytosine deamination is effected by bisulfite or apolipoprotein B mRNA editing enzyme, catalytic polypeptide-like (APOBEC). 28. The method of any one of embodiments 1-26, wherein the segment at the 3' end of individual extension primers comprises the sequence CGCGCGG, CGCGCGA, CGCGCGT, CGCGCGC, CGGCGCGG, CGGCGCGA, CGGCGCGT, CGGCGCGC, CGCGGCGG, CGCGGCGA, CGCGGCGT, CGCGGCGC, CGGCGGCGG, CGGCGGCGA, CGGCGGCGT, or CGGCGGCGC. 29. The method of any one of embodiments 1-26, wherein the segment at the 3' end of individual extension primers comprises the sequence CGCGCGG. 30. The method of any one of embodiments 1-26, wherein at least one of the first and second primers of the primer pair comprises a barcode sequence, an amplification primer binding sequence, a sequencing primer binding sequence, or combinations thereof 31. The method of any one of embodiments 1-26, wherein the sample comprises cell-free polynucleotides. 32. The method of any one of embodiments 1-26, wherein the sample comprises genomic polynucleotides. 33. The method of any one of embodiments 1-26, wherein the sample is obtained from a formalin-fixed paraffin-embedded (FFPE) tissue sample. 34. The method of any one of embodiments 1-26, wherein the sample is obtained from a frozen tissue sample. 35. The method of any one of embodiments 1-26, wherein the sample is obtained from a biological fluid. 36. The method of any one of embodiments 1-26, wherein the transposase is a Tn transposase, an MuA transposase, or a Vibhar transposase. 37. The method of any one of embodiments 1-36, wherein the transposase is a Tn transposase selected from Tn3, Tn5, Tn7, and Tn10. 38. The method of any one of embodiments 1-26, wherein individual transposomes comprise a dimer of monomers, which monomers comprise a transposase and a transposon sequence. 39. The method of any one of embodiments 1-26, wherein the amplifying of (d) is effected by a Hot-Start enzyme. 40. The method of any one of embodiments 1-39, wherein the Hot-Start enzyme is a Hot-Start polymerase. 41. A kit for generating extension products of a target polynucleotide, comprising: (a) a transposase; (b) a transposon sequence having a transposon element; (c) an extension primer comprising: (i) a segment at a 3' end exhibiting sequence complementarity to the target polynucleotide, and (ii) a segment at a 5' end lacking sequence complementarity to the target polynucleotide; (d) a Hot-Start polymerase; and (e) instructions for use of the kit for generating extension products of the target polynucleotide. 42. The kit of any one of embodiments 1-41, wherein the instructions of (d) comprise: (i) contacting the target polynucleotide with a transposome to yield a tagged fragment, said transposome comprising the transposase complexed with the transposon sequence, wherein the tagged fragment comprises the transposon sequence joined to the 5' end of a segment of the target polynucleotide; (ii) subjecting the tagged fragment to an extension reaction using said extension primer to yield said extension products, wherein a given extension product comprises (i) the tagged fragment sequence and a complement of the extension primer sequence, or (ii) a complement of the tagged fragment sequence and the extension primer sequence. 43. The kit of any one of embodiments 1-41, further comprising a primer pair, wherein said primer pair includes a first primer comprising the transposon sequence or a portion thereof and a second primer comprising the sequence of the segment at the 5' end of the extension primer or a portion thereof 44. The kit of any one of embodiments 1-43, wherein at least one of the first and second primers comprises a barcode sequence, amplification primer binding sequence, sequencing primer binding sequence, or combinations thereof 45. The kit of any one of embodiments 1-43, wherein the instructions of (d) further comprises: (iii) amplifying the extension products using the primer pair to yield a plurality of amplification products, wherein individual amplification products comprise a single copy of a transposon sequence or a complement thereof 46. The kit of any one of embodiments 1-41, wherein the transposase is a Tn transposase, an MuA transposase, or a Vibhar transposase. 47. The kit of any one of embodiments 1-46, wherein the transposase is a Tn transposase selected from Tn3, Tn5, Tn7, and Tn10. 48. The kit of any one of embodiments 1-41, wherein the transposon comprises methylated cytosines. 49. The kit of any one of embodiments 1-41, further comprising at least one of bisulfate, APOBEC, and DNMT1. 50. A reaction mixture for forming extension products, comprising: (a) a transposome comprising a transposase complexed with a transposon sequence; (b) a target polynucleotide; (c) an extension primer comprising: (i) a segment at a 3' end exhibiting sequence complementarity to the target polynucleotide, and (ii) a segment at a 5' end lacking sequence complementarity to the target polynucleotide; and (d) a Hot-Start polymerase. 51. The reaction mixture of any one of embodiments 1-50, further comprising a primer pair, wherein said primer pair includes a first primer comprising the transposon sequence or a portion thereof and a second primer comprising the sequence of the segment at the 5' end of the extension primer or a portion thereof 52. The reaction mixture of any one of embodiments 1-51, wherein at least one of the first and second primers comprises a barcode sequence, amplification primer binding sequence, sequencing primer binding sequence, or combinations thereof 53. The reaction mixture of any one of embodiments 1-50, wherein the target polynucleotide is a cell-free polynucleotide. 54. The reaction mixture of any one of embodiments 1-50, wherein the target polynucleotide is a genomic polynucleotide. 55. The reaction mixture of any one of embodiments 1-50, wherein the target polynucleotide is obtained from a formalin-fixed paraffin-embedded (FFPE) tissue sample. 56. The reaction mixture of any one of embodiments 1-50, wherein the target polynucleotide is obtained from a frozen tissue sample. 57. The reaction mixture of any one of embodiments 1-50, wherein the target polynucleotide is obtained from a biological fluid. 58. The reaction mixture of any one of embodiments 1-50, wherein the transposon comprises methylated cytosines. 59. The reaction mixture of any one of embodiments 1-50, wherein the transposome complex comprises a homodimer of monomers, which monomers comprise a transposase complexed with a transposon sequence. 60. The reaction mixture of any one of embodiments 1-50, wherein the transposase is a Tn transposase, an MuA transposase, or a Vibhar transposase. 61. The reaction mixture of any one of embodiments 1-60, wherein the transposase is a Tn transposase selected from Tn3, Tn5, Tn7, and Tn10. 62. A system comprising: (a) a computer configured to receive a user request to perform a nucleic acid detection reaction on a polynucleotide sample; (b) one or more processors configured to execute commands that effect an amplification unit to perform a nucleic acid amplification reaction on the sample or a portion thereof in response to the user request, wherein the amplification reaction comprises the steps of: (i) contacting the polynucleotide sample with transposomes to yield a plurality of tagged fragments, individual transposomes comprising a transposase complexed with a transposon sequence, wherein a given tagged fragment of the plurality comprises a transposon sequence joined to the 5' end of a segment of a given polynucleotide of the polynucleotide sample; (ii) subjecting said plurality of tagged fragments to an extension reaction using extension primers to yield extension products, individual extension primers having a segment at a 3' end exhibiting sequence complementarity to a tagged fragment and a segment at a 5' end lacking sequence complementarity to the tagged fragment, and wherein a given extension product comprises (i) a tagged fragment sequence and a complement of a primer sequence, or (ii) a complement of a tagged fragment sequence and a primer sequence; and (iii) amplifying the extension products using a primer pair to yield amplification products comprising a single copy of a transposon sequence or a complement thereof, wherein the primer pair includes a first primer comprising the transposon sequence, or a portion thereof, and a second primer comprising the sequence of the segment at the 5' end of the extension primer, or a portion thereof.

EXAMPLES

The following examples are given for the purpose of illustrating various embodiments of the disclosure and are not meant to limit the present disclosure in any fashion. The present examples, along with the methods described herein, are exemplary and are not intended as limitations on the scope of the disclosure.

Example 1: Methylation Profiling with 'CG' Tandem Primer 5 ml peripheral blood is collected with EDTA anticoagulant tubes and centrifuged at 1,350×g for 12 minutes at room temperature twice with new tubes. Supernatant is aliquoted to 2-ml tubes and centrifuged at 13,500×g for 5 minutes. The plasma cell-free DNAs is extracted using QIAamp DNA Blood Midi Kit.

Equal molar DNA oligos transposon Read2-ME: $^m$CAG-A$^m$CGTGTG$^m$CT$^m$CTT$^m$C$^m$C GAT$^m$CTA-GATGTGTATAAGAGA$^m$CAG (SEQ ID NO: 1) and ME': (5phos)-CTGTCTCTTATACACATCT (SEQ ID NO: 2) are annealed in the presence of 1×STE (10 mM Tris pH 8.0, 50 mM NaCl, 1 mM EDTA) by incubating at 95° C. for 1 minute then cooling down to room temperature. Double-stranded transposons are then incubated with Tn5 transposase at 1.2:1 molar ratio at room temperature for 30 minutes to form transposome complexes.

Cell-free DNA is incubated with the transposome complexes at 55° C. for 15 minutes. Bisulfite conversion is performed on fragmented double-strand DNA by using EZ DNA Methylation-Direct Kits (Zymo Research). After this, the converted DNA, along with 100 ng carrier tRNA, is purified with DNA Clean-up & Concentration (Zymo Research). In the first primer extension, fragmented double-strand DNA is incubated in a 20 uL reaction with 1×Q5 Reaction Buffer, 0.02 U/uL Q5 Hot Start High-Fidelity DNA Polymerase (New England BioLabs Inc), 200 uM dNTPs, and 0.5 uM primer A: ACACTCTTTCCCTA-CACGACGCTCTTCCGA TCTDDDDCGCGCGG (SEQ ID NO: 3). The reaction is subjected to the following conditions: 95° C. for 3 min, followed by 50° C. for 2 min and 72° C. for 1 min. In the second step, the amplicon is exponentially amplified in a 50 uL reaction by adding 30 uL solution containing 1×Q5 Reaction buffer, 0.04 U/uL Q5 Hot Start High-Fidelity DNA Polymerase (New England Bio-Labs Inc), 200 uM dNTPs and 1 uM primer B: AATGA-TACGGCGACCACCGAGATCTACACTCTTTCCCT ACACGACGCTCTTCCGATCT (SEQ ID NO: 4) and 1 uM primer C: CAAGCAGAAGACGGCATACGAGA TGTGACTGGAGTTCAGACGTGTGCTCTTCCGATCT (SEQ ID NO: 5). The reaction is subjected to the following cycling conditions: 95° C. for 3 min, 17 cycles for 95° C. for 30 sec, 65° C. for 30 sec, 72° C. for 1 min and a final cycle of 72° C. for 5 min. The resulting amplified product is purified to serve as library for sequencing on Illumina HiSeq X or NovaSeq sequencer for paired-end reads.

Example 2: Targeted Methylation Profiling 5 ml peripheral blood is collected with EDTA anticoagulant tubes and centrifuged at 1,350×g for 12 minutes at room temperature twice with new tubes. Supernatant is aliquoted to 2-ml tubes and centrifuged at 13,500×g for 5 minutes. The plasma cell-free DNAs is extracted using QIAamp DNA Blood Midi Kit.

Equal molar DNA oligos transposon Read2-ME: $^m$CAG-A$^m$CGTGTG$^m$CT$^m$CTT$^m$C$^m$C GAT$^m$CTA-GATGTGTATAAGAGA$^m$CAG (SEQ ID NO: 1) and ME': (5phos)-CTGTCTCTTATACACATCT (SEQ ID NO: 2) are annealed in the presence of 1×STE (10 mM Tris pH 8.0, 50 mM NaCl, 1 mM EDTA) by incubating at 95° C. for 1 minute then cooling down to room temperature. Double-stranded transposons are then incubated with Tn5 transposase at 1.2:1 molar ratio at room temperature for 30 minutes to form transposome complexes.

Cell-free DNA is incubated with transposome complexes at 55° C. for 15 minutes. SDS is added to the reaction at final 0.02% and incubated at 70° C. for 10 min. In the first primer extension, fragmented double-strand DNA is incubated in a 20 uL reaction with 1×Q5 Reaction Buffer, 0.02 U/uL Q5 Hot Start High-Fidelity DNA Polymerase (New England BioLabs Inc), 200 uM dNTPs, and primer mixture, which all share the following sequence at 5' end, A$^m$CA$^m$-CT$^m$CTTT$^m$C$^m$C$^m$CTA$^m$CA$^m$CGA$^m$CG$^m$CT$^m$CTT$^m$C$^m$C-GAT$^m$CT (SEQ ID NO: 6). The reaction is subjected to the following conditions: 95° C. for 3 min, followed by 50° C. for 2 min and 72° C. for 1 min. Then the reaction is added with final 1×Dnmt1 reaction buffer, 0.15 uL 160 uM SAM, 0.15 uL 100 ug/ml BSA, and 2 uL 2 U/ul Dnmt1 (New England BioLabs Inc), then incubated at 37° C. for 3 hours.

Bisulfite conversion is then performed by using EZ DNA Methylation-Direct Kits (Zymo Research). After this, the converted DNA along with 100 ng carrier tRNA is purified with DNA Clean-up & Concentration (Zymo Research).

Next, the amplicon is exponentially amplified in a 50 uL reaction by adding 30 uL solution containing 1×Q5 Reaction buffer, 0.04 U/uL Q5 Hot Start High-Fidelity DNA Polymerase (New England BioLabs Inc), 200 uM dNTPs and 1 uM primer B: AATGATACGG CGACCACCGAGATCTA-CACTCTTTCCCTACACGACGCTCTTCCGATCT (SEQ ID NO: 4) and 1 uM primer C: CAAGCAGAAGACGG-CATACGAGATGTGACTGGAGTTCAGACGTGTGCTC TTCCGATCT (SEQ ID NO: 5). The reaction is subjected to the following cycling conditions: 95° C. for 3 min, 17 cycles for 95° C. for 30 sec, 65° C. for 30 sec, 72° C. for 1 min and a final cycle of 72° C. for 5 min. The resulting amplified product is purified to serve as library for sequencing on Illumina HiSeq X or NovaSeq sequencer for paired-end reads.

Example 3: Target Gene Panel Sequencing 5 ml peripheral blood is collected with EDTA anticoagulant tubes and centrifuged at 1,350×g for 12 minutes at room temperature twice with new tubes. Supernatant is aliquoted to 2-ml tubes and centrifuged at 13,500×g for 5 minutes. The plasma cell-free DNAs are extracted using QIAamp DNA Blood Midi Kit.

Equal molar DNA oligos transposon Read2-ME: CAGACGTGTGCTCTTCCGATCT AGATGTGTATAAGAGACAG (SEQ ID NO: 7) and ME': (5phos)-CTGTCTCTTATACACATCT (SEQ ID NO: 2) are annealed in the presence of 1×STE (10 mM Tris pH 8.0, 50 mM NaCl, 1 mM EDTA) by incubating at 95° C. for 1 minute then cooling down to room temperature. Double-stranded transposons are then incubated with Tn5 transposase at 1.2:1 molar ratio at room temperature for 30 minutes to form transposome complexes.

Cell-free DNA is incubated with transposome complexes at 55° C. for 15 minutes. SDS is added to the reaction at final 0.02% and incubated at 70° C. for 10 min. In the first primer extension, fragmented double-strand DNA is incubated in a 20 uL reaction with 1×Q5 Reaction Buffer, 0.02 U/uL Q5 Hot Start High-Fidelity DNA Polymerase (New England BioLabs Inc), 200 uM dNTPs, and primer mixture for gene of interests, which all share the following sequence at 5' end: ACACTCTTTCCCTACACGACGCTCTTCCGATCT (SEQ ID NO: 8). The reaction is subjected to the following conditions: 95° C. for 3 min, followed by 50° C. for 2 min and 72° C. for 1 min. Next, the amplicon is exponentially amplified in a 50 uL reaction by adding 30 uL solution containing 1×Q5 Reaction buffer, 0.04 U/uL Q5 Hot Start High-Fidelity DNA Polymerase (New England BioLabs Inc), 200 uM dNTPs and 1 uM primer B: AATGATACGGCGACCACCGAGATCTAC ACTCTTTCCCTA-CACGACGCTCTTCCGATCT (SEQ ID NO: 4) and 1 uM primer C: CAAGCAGAAGACGG CAT-ACGAGATGTGACTGGAGTTCA-GACGTGTGCTCTTCCGATCT (SEQ ID NO: 5). The reaction was subjected to the following cycling conditions: 95° C. for 3 min, 17 cycles for 95° C. for 30 sec, 65° C. for 30 sec, 72° C. for 1 min and a final cycle of 72° C. for 5 min. The resulting amplified product is purified to serve as library for sequencing on Illumina HiSeq X or NovaSeq sequencer for paired-end reads.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of forming amplification products of a target polynucleotide, comprising:
   (a) contacting a target polynucleotide present in a polynucleotide sample with transposomes to yield a plurality of tagged fragments, wherein individual transposomes comprise a transposase complexed with a transposon sequence having a transposon element, wherein a given tagged fragment of the plurality comprises the transposon sequence joined to the 5' end of a segment of the target polynucleotide;
   (b) subjecting said plurality of tagged fragments to an extension reaction using extension primers to yield extension products, wherein individual extension primers have a segment at a 3' end exhibiting sequence complementarity to a tagged fragment and a segment at a 5' end lacking sequence complementarity to the tagged fragment, and wherein a given extension product comprises (i) a sequence of the given tagged fragment and a complement of an extension primer sequence, or (ii) a complement of the given tagged fragment sequence and the extension primer sequence, wherein the transposon sequence or the extension primer comprises a methylated cytosine, wherein the methylated cytosine stabilizes a primer-dimer formed by the extension primers; and
   (c) amplifying the extension products using a primer pair to yield amplification products, wherein the primer pair includes a first primer comprising the transposon sequence or a portion thereof and a second primer comprising the sequence of the segment at the 5' end of the extension primer or a portion thereof, wherein individual amplification products comprise a single copy of the transposon sequence or a complement thereof.

2. The method of claim 1, wherein the segment at the 3' end of individual extension primers lacks sequence complementarity to the transposon sequence.

3. The method of claim 1, wherein the segment at the 3' end of individual extension primers comprises a gene specific sequence.

4. The method of claim 3, wherein the extension primers comprise a mixture of gene specific extension primers.

5. The method of claim 4, wherein the extension primers share an identical segment at the 5' end.

6. The method of claim 1, wherein the extension products comprise hemi-methylated double-stranded DNA.

7. The method of claim 6, further comprising, subsequent to (b), subjecting said extension products comprising hemi-methylated double-stranded DNA to a methylation reaction to yield extension products comprising fully methylated double-stranded DNA.

8. The method of claim 7, wherein methylation is effected by methyl transferase activity.

9. The method of claim 7, wherein methylation is effected by a DNA methyltransferase enzyme.

10. The method of claim 9, wherein the DNA methyltransferase enzyme is DNA (cytosine-5)-methyltransferase 1 (DNMT1).

11. The method of claim 10, further comprising, prior to (c), subjecting said extension products comprising fully methylated double-stranded DNA to cytosine deamination to convert unmethylated cytosines to uracil.

12. The method of claim 11, wherein cytosine deamination is effected by bisulfite or apolipoprotein B mRNA editing enzyme, catalytic polypeptide-like (APOBEC).

13. The method of claim 1, wherein at least one of the first and second primers of the primer pair comprises a barcode sequence, an amplification primer binding sequence, a sequencing primer binding sequence, or combinations thereof.

14. The method of claim 1, wherein the polynucleotide is a cell-free polynucleotide.

15. The method of claim 1, wherein the polynucleotide is a genomic polynucleotide.

16. The method of claim 1, wherein the polynucleotide sample is obtained from a formalin-fixed paraffin-embedded (FFPE) tissue sample.

17. The method of claim 1, wherein the polynucleotide sample is obtained from a frozen tissue sample.

18. The method of claim 1, wherein the polynucleotide sample is obtained from a biological fluid.

19. The method of claim 1, wherein the transposon sequence comprises methylated cytosines.

20. The method of claim 1, wherein the transposase is a Tn transposase, an MuA transposase, or a Vibhar transposase.

21. The method of claim 20, wherein the transposase is a Tn transposase selected from Tn3, Tn5, Tn7, and Tn10.

22. The method of claim 1, wherein individual transposomes comprise a dimer of monomers, which monomers comprise a transposase complexed with a transposon sequence.

23. The method of claim 1, wherein the amplifying of (c) is effected by a Hot-Start enzyme.

24. The method of claim 23, wherein the Hot-Start enzyme is a Hot-Start polymerase.

* * * * *